United States Patent
Hansen et al.

(10) Patent No.: US 6,676,924 B2
(45) Date of Patent: *Jan. 13, 2004

(54) CDR-GRAFTED TYPE III ANTI-CEA HUMANIZED MOUSE MONOCLONAL ANTIBODIES

(75) Inventors: Hans J. Hansen, Mystic Island, NJ (US); Kathryn L. Armour, Scotland (GB)

(73) Assignee: Immunomedics, Inc., Morris Plains, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/253,794

(22) Filed: Feb. 22, 1999

(65) Prior Publication Data

US 2002/0018750 A1 Feb. 14, 2002

Related U.S. Application Data

(62) Division of application No. 08/318,157, filed on Oct. 5, 1994, now Pat. No. 5,874,540.

(51) Int. Cl.[7] ........................ A61K 39/395; C07K 16/00
(52) U.S. Cl. ................ 424/1.49; 424/133.1; 424/174.1; 424/178.1; 424/181.1; 424/183.1; 530/387.3; 530/388.85; 530/391.1; 530/391.3; 530/391.7
(58) Field of Search ........................... 424/133.1, 174.1, 424/178.1, 181.1, 183.1, 1.49; 530/387.3, 388.85, 391.1, 391.7, 391, 3

(56) References Cited

U.S. PATENT DOCUMENTS

| | | |
|---|---|---|
| 4,818,709 A | 4/1989 | Primus et al. .............. 436/518 |
| 5,081,235 A | 1/1992 | Shively et al. ................ 536/27 |
| 5,530,101 A | 6/1996 | Queen et al. ............. 530/387.3 |

FOREIGN PATENT DOCUMENTS

| | | |
|---|---|---|
| EP | 0 239 400 | 9/1987 |
| EP | 0 323 805 A2 | 7/1989 |
| EP | 0 323 806 | 12/1989 |
| WO | WO 92/01059 | 1/1992 |
| WO | WO 92/11018 | * 7/1992 |

OTHER PUBLICATIONS

Primus, et al., "Immunological Heterogeneity of Carcinoembryonic . . . ", Cancer Research, 43:686–92, Feb. 1983.
Hansen, et al., "Characterization of Second–Generation Monoclonal . . . ", Cancer, 71(11):3478–85, Jun. 1993.
Losman, et al., Mimicry of a Carcinoembryonic Antigen Epitope . . . , Int. J. Cancer, 56:580–84, 1994.
Sharkey, et al., Cancer 71(6):2082–2096 (1993).
Riechmann, et al. Nature 332:323–327 (1988).
Queen, et al., PNAS 86:10029–10033 (1989).
Blumenthal, et al, Cancer Res 52(21):6036–6044 (1992).

* cited by examiner

Primary Examiner—David Saunders
(74) Attorney, Agent, or Firm—Foley & Lardner

(57) ABSTRACT

A humanized monoclonal antibody, comprising the complementarity-determining regions of a parental murine Class III, anti-CEA monoclonal antibody engrafted to the framework regions of a heterologous antibody, wherein the humanized monoclonal antibody retains the binding specificity of, but is less immunogenic in a heterologous host than, the parental murine monoclonal antibody A preferred murine Class III, anti-CEA monoclonal antibody is the MN-14 antibody and the preferred heterologous antibody is from a human. Also provided are DNA constructs and vectors for producing the humanized monoclonal antibodies, and diagnostic and therapeutic conjugates using same.

27 Claims, 16 Drawing Sheets

```
            PNA  N T        B     A              A B B               T H
            VSL  S T        S     L              L S S               T P
            UPU  P H        M     W              W T M               H H
            2rl  r 1        2     2              2 X 2               1 1
    GAAATTCAGCTGACCCAGTCTCCACAAAATGATGTCCACATCAGTGGGAGACAGGGTCAGC  +60
    ---------+---------+---------+---------+---------+---------+
    CTTTAAGTCGACTGGGTCAGAGAGGTGTTTTACTACAGTGTAGTCACCCTCTGTCCCAGTCG
     e  i  q  l  t  q  s  h  k  m  m  s  t  s  v  g  d  r  v  s

R      F          E AS    A        BPB    E EAS
      S       S      O          C PC    L        SPS    C CPC
      F  BHH  A      K          R YR    W        MAA  R PYR
      A  SAA  1      1          2 11    2        211  2 111
      N  PEE
         113
    ATCACCTGCAAGGCCAGTCAGGATGTGGGTACTTCTGTAGCCTGGTATCAACAGAGACCA  +120
    ---------+---------+---------+---------+---------+---------+
    TAGTGGACGTTCCGGTCAGTCCTACACCCATGAAGACATCGGACCATAGTTGTCTCTGGT
     i  t  c  k  a  s  q  d  v  g  t  s  v  a  w  y  q  q  r  p

E    F                      NSH     HF   MPDD
              C    O                      CCP     NI   BLPP
              O    K                      IRA     FN   OENN
              D    1                      112     11   1121
    GGACAATCTCCTAAACTACTGATTTACTGGACATCCACCCGGCACACTGGAGTCCCTGAT  +180
    ---------+---------+---------+---------+---------+---------+
    CCTGTTAGAGGATTTGATGACTAAATGACCTGTAGGTGGGCCGTGTGACCTCAGGGACTA
     g  q  s  p  k  l  l  i  y  w  t  s  t  r  h  t  g  v  p  d
```

FIG. 2A

```
                                       F         H                                              B
                                       I         P                                              B
                                       N         H                                              V
                                       1         1                                              2
     CGCTTCACAGGCAGTGTGTCTGGGACAGATTTCACTCTCACCATTACCAATGTGCAGTCT   240
     ---------+---------+---------+---------+---------+---------+
     GCGAAGTGTCCGTCACACAGACCCTGTCTAAAGTGAGAGTGGTAATGGTTACACGTCAGA
      r  f  g  s  v  s  g  t  d  f  t  l  t  i  t  n  v  q  s

B         M              M  M                                B  N
          B         B              N  N                                A  L
          S         O              L  L                                N  A
          1         2              1  1                                1  4
     GAAGACTTGGCAGAGATTATTTCTGT CAGCAATATAGCCTCTATCGGTCGT TCGGTGGAGGC   300
     ---------+---------+---------+---------+---------+---------+
     CTTCTGAACCGTCTAATAAAGACA GTCGTTATATCGGAGATAGCCAGC AAGCCACCTCCG
      e  d  l  a  d  y  f  c  q  q  y  s  l  y  r  s  f  g  g  g

ACCAAAACTGGAGATCAAA          318
     ---------+---------
     TGGTTTTGACCTCTAGTTT
      t  k  l  e  i  k

BMDD
            SBPP
            RONN
            1121
            ///
```

|  | FR1 | CDR1 | FR2 |
|---|---|---|---|
|  | 24 27 30 | | 48 |
| Murine | EVKLLESGGGLVQSGGSLKLSCAASGFDFT | TYWMS | WVRQAPGKGLEWIG |
| NEWMVh | Q-Q-Q---P---RPSQT-S-T-TV--ST-S | ----- | ----P---R----- |
| NMHuVh | Q-Q-Q---P---RPSQT-S-T-T------- | ----- | ----P---R----- |
| NMHUVhTLY | Q-Q-Q---P---RPSQT-S-T-T------- | ----- | ----P---R----- |
| NMHUVhKRSE | Q-Q-Q---P---RPSQT-S-T-T------- | ----- | ----P---R----- |
| NMHUVhKFIVS | Q-Q-Q---P---RPSQT-S-T-T------- | ----- | ----P---R----- |
| KOLVh | --Q-V---V---V--P-R---SS---I-S | ----- | ------------- |
| KLHuVh | --Q-V---V---V--P-R---SS------ | ----- | ------------VA |
| KLHuVhAIG | --Q-V---V---V--P-R---S-------- | ----- | ------------VA |
| KLHuVhAIGA | --Q-V---V---V--P-R---S-------- | ----- | ------------- |
| KLHuVhAIGAY | --Q-V---V---V--P-R---S-------- | ----- | ------------- |

FIG. 6B

```
              CDR2                FR3
              66  71  74 77 79    82              94
              EIHPDSSTINYAPSLKD   KFIVSRDNAKNTLYLQMSKVRSEDTALYYCAS
Murine        EIHPDSSTINYAPSLKD   KFIVSRDNAKNTLYLQMSKVRSEDTALYYCAS
NEWMVh        ----------------   RVTMLV-TS--QFS-RL-S-TAA---V----R
NMHuVh        ----------------   RVTML--TS--QFS-RL-S-TAA---V-----
NMHUVhTLY     ----------------   RVTML--TS----RL-S-TAA---V-----
NMHUVhKRSE    ----------------   RVTML--TS--QFS-RL-------V-----
NMHUVhKFIVS   ----------------   -------TS--QFS-RL-S-TAA---V-----
KOLVh         ----------------   R-TI---S----F---DSL-P---GV-F---R
KLHuVh        ----------------   R-TI---S----F---DSL-P---GV-F----
KLHuVhAIG     ----------------   R-TI---S----F---DSL-P---GV-F----
KLHuVhAIGA    ----------------   R-TI--------F---DSL-P---GV-F----
KLHuVhAIGAY   ----------------   R-TI--------F---DSL-P---GV-F----
```

FIG. 6C

| | CDR3 | FR4 | |
|---|---|---|---|
| Murine | LYFGFPWFAY | WGQGTPVTVSA | |
| NEWMVh | ---------- | ---------- | S |
| NMHuVh | ---------- | -------T--- | S |
| NMHUVhTLY | ---------- | -------T--- | S |
| NMHUVhKRSE | ---------- | -------T--- | S |
| NMHUVhkFIVS | ---------- | -------T--- | S |
| KOLVh | ---------- | -------T--- | S |
| KLHuVh | ---------- | ---------- | S |
| KLHuVhAIG | ---------- | ---------- | S |
| KLHuVhAIGA | ---------- | ---------- | S |
| KLHuVhAIGAY | ---------- | ---------- | S |

FIG. 8

SEQUENCE LISTING (1) GENERAL INFORMATION:

(iii) NUMBER OF SEQUENCES: 58

(2) INFORMATION FOR SEQ ID NO: 1:

(i) SEQUENCE CHARACTERISTICS:
      (A) LENGTH: 357 base pairs
      (B) TYPE: nucleic acid
      (C) STRANDEDNESS: double
      (D) TOPOLOGY: linear (ii) MOLECULE TYPE: DNA (genomic)

(ix) FEATURE:
      (A) NAME/KEY: CDS
      (B) LOCATION: 1..357

(xi) SEQUENCE DESCRIPTION: SEQ ID NO: 1:

```
GAG GTG AAG CTT CTC GAG TCT GGA GGT GGC CTG GTG CAG TCT GGA GGA      48
Glu Val Lys Leu Leu Glu Ser Gly Gly Gly Leu Val Gln Ser Gly Gly
 1               5                  10                  15

TCC CTG AAA CTC TCC TGT GCA GCC TCA GGA TTC GAT TTT ACT ACA TAT      96
Ser Leu Lys Leu Ser Cys Ala Ala Ser Gly Phe Asp Phe Thr Thr Tyr
            20                  25                  30

TGG ATG AGT TGG GTC CGG CAG GCT CCA GGG AAA GGC CTA GAA TGG ATT     144
Trp Met Ser Trp Val Arg Gln Ala Pro Gly Lys Gly Leu Glu Trp Ile
        35                  40                  45

GGA GAA ATT CAT CCA GAT AGC AGT ACG ATT AAC TAT GCG CCG TCT CTA     192
Gly Glu Ile His Pro Asp Ser Ser Thr Ile Asn Tyr Ala Pro Ser Leu
    50                  55                  60

AAG GAT AAA TTC ATC GTC TCC AGA GAC AAC GCC AAA AAT ACG CTG TAC     240
Lys Asp Lys Phe Ile Val Ser Arg Asp Asn Ala Lys Asn Thr Leu Tyr
65                  70                  75                  80

CTG CAA ATG AGC AAA GTG AGA TCT GAG GAC ACA GCC CTT TAT TAC TGT     288
Leu Gln Met Ser Lys Val Arg Ser Glu Asp Thr Ala Leu Tyr Tyr Cys
```

```
                    85                   90                   95
GCA AGC CTT TAC TTC GGC TTC CCC TGG TTT GCT TAT TGG GGC CAA GGG        336
Ala Ser Leu Tyr Phe Gly Phe Pro Trp Phe Ala Tyr Trp Gly Gln Gly
            100                 105                 110

ACT CCG GTC ACT GTC TCT GCA                                            357
Thr Pro Val Thr Val Ser Ala
        115

(2) INFORMATION FOR SEQ ID NO: 2:

(i) SEQUENCE CHARACTERISTICS:
        (A) LENGTH: 119 amino acids
        (B) TYPE: amino acid
        (D) TOPOLOGY: linear (ii) MOLECULE TYPE: protein (xi) SEQUENCE DESCRIPTION: SEQ ID NO: 2:

Glu Val Lys Leu Leu Glu Ser Gly Gly Gly Leu Val Gln Ser Gly Gly
 1               5                  10                  15

Ser Leu Lys Leu Ser Cys Ala Ala Ser Gly Phe Asp Phe Thr Thr Tyr
            20                  25                  30

Trp Met Ser Trp Val Arg Gln Ala Pro Gly Lys Gly Leu Glu Trp Ile
        35                  40                  45

Gly Glu Ile His Pro Asp Ser Ser Thr Ile Asn Tyr Ala Pro Ser Leu
    50                  55                  60

Lys Asp Lys Phe Ile Val Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
            85                  90                  95

Ala Ser Leu Tyr Phe Gly Phe Pro Trp Phe Ala Tyr Trp Gly Gln Gly
            100                 105                 110

Thr Pro Val Thr Val Ser Ala
        115

(2) INFORMATION FOR SEQ ID NO: 3:

(i) SEQUENCE CHARACTERISTICS:
        (A) LENGTH: 318 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..318

(xi) SEQUENCE DESCRIPTION: SEQ ID NO: 3:

GAA ATT CAG CTG ACC CAG TCT CAC AAA ATG ATG TCC ACA TCA GTG GGA         48
Glu Ile Gln Leu Thr Gln Ser His Lys Met Met Ser Thr Ser Val Gly
120                 125                 130                 135

GAC AGG GTC AGC ATC ACC TGC AAG GCC AGT CAG GAT GTG GGT ACT TCT         96
Asp Arg Val Ser Ile Thr Cys Lys Ala Ser Gln Asp Val Gly Thr Ser
            140                 145                 150

GTA GCC TGG TAT CAA CAG AGA CCA GGA CAA TCT CCT AAA CTA CTG ATT        144
Val Ala Trp Tyr Gln Gln Arg Pro Gly Gln Ser Pro Lys Leu Leu Ile
            155                 160                 165

TAC TGG ACA TCC ACC CGG CAC ACT GGA GTC CCT GAT CGC TTC ACA GGC        192
Tyr Trp Thr Ser Thr Arg His Thr Gly Val Pro Asp Arg Phe Thr Gly
        170                 175                 180
```

```
AGT GTG TCT GGG ACA GAT TTC ACT CTC ACC ATT ACC AAT GTG CAG TCT        240
Ser Val Ser Gly Thr Asp Phe Thr Leu Thr Ile Thr Asn Val Gln Ser
    185                 190                 195

GAA GAC TTG GCA GAT TAT TTC TGT CAG CAA TAT AGC CTC TAT CGG TCG        288
Glu Asp Leu Ala Asp Tyr Phe Cys Gln Gln Tyr Ser Leu Tyr Arg Ser
200                 205                 210                 215

TTC GGT GGA GGC ACC AAA CTG GAG ATC AAA                                318
Phe Gly Gly Gly Thr Lys Leu Glu Ile Lys
                220                 225
```

(2) INFORMATION FOR SEQ ID NO: 4:

(i) SEQUENCE CHARACTERISTICS:
        (A) LENGTH: 106 amino acids
        (B) TYPE: amino acid
        (D) TOPOLOGY: linear (ii) MOLECULE TYPE: protein (xi) SEQUENCE DESCRIPTION: SEQ ID NO: 4:

```
Glu Ile Gln Leu Thr Gln Ser His Lys Met Met Ser Thr Ser Val Gly
1               5                   10                  15

Asp Arg Val Ser Ile Thr Cys Lys Ala Ser Gln Asp Val Gly Thr Ser
                20                  25                  30

Val Ala Trp Tyr Gln Gln Arg Pro Gly Gln Ser Pro Lys Leu Leu Ile
            35                  40                  45

Tyr Trp Thr Ser Thr Arg His Thr Gly Val Pro Asp Arg Phe Thr Gly
        50                  55                  60

Ser Val Ser Gly Thr Asp Phe Thr Leu Thr Ile Thr Asn Val Gln Ser
65                  70                  75                  80

Glu Asp Leu Ala Asp Tyr Phe Cys Gln Gln Tyr Ser Leu Tyr Arg Ser
                85                  90                  95

Phe Gly Gly Gly Thr Lys Leu Glu Ile Lys
                100                 105
```

(2) INFORMATION FOR SEQ ID NO: 5:

(i) SEQUENCE CHARACTERISTICS:
        (A) LENGTH: 119 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 5:

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Asn Asp
                20                  25                  30

Tyr Tyr Thr Trp Val Arg Gln Pro Pro Gly Arg Gly Leu Glu Trp Ile
            35                  40                  45

Gly Tyr Val Phe Tyr His Gly Thr Ser Asp Thr Thr Pro Ser Leu
        50                  55                  60

Arg Ser Arg Val Thr Met Leu Val Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Asn Leu Ile Ala Gly Cys Trp Ile Asp Val Trp Gly Gln Gly
                100                 105                 110
```

```
Thr Thr Val Thr Val Ser Ser
            115

(2) INFORMATION FOR SEQ ID NO: 6:

(i) SEQUENCE CHARACTERISTICS:
        (A) LENGTH: 107 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 6:

Asp Ile Gln Leu Thr Gln Ser Pro Ser Ser Leu Ser Ala Ser Val Gly
1               5                  10                  15

Asp Arg Val Thr Ile Thr Cys Gln Ala Ser Gln Asp Ile Ile Lys Tyr
                20                  25                  30

Leu Asn Trp Tyr Gln Gln Lys Pro Gly Lys Ala Pro Lys Leu Leu Ile
            35                  40                  45

Tyr Glu Ala Ser Asn Leu Gln Ala Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Gln Ser Leu Pro Tyr
                85                  90                  95

Thr Phe Gly Gln Gly Thr Lys Val Glu Ile Lys
            100                 105

(2) INFORMATION FOR SEQ ID NO: 7:

(i) SEQUENCE CHARACTERISTICS:
        (A) LENGTH: 126 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 7:

Glu Val Gln Leu Val Glu Ser Gly Gly Gly Val Val Gln Pro Gly Arg
1               5                  10                  15

Ser Leu Arg Leu Ser Cys Ser Ser Gly Phe Ile Phe Ser Ser Tyr
                20                  25                  30

Ala Met Tyr Trp Val Arg Gln Ala Pro Gly Lys Gly Leu Glu Trp Val
            35                  40                  45

Ala Ile Ile Trp Asp Asp Gly Ser Asp Gln His Tyr Ala Asp Ser Val
50                  55                  60

Lys Gly Arg Phe Thr Ile Ser Arg Asp Asn Ser Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg Asp Gly Gly His Gly Phe Cys Ser Ser Ala Ser Cys Phe Gly
            100                 105                 110

Pro Asp Tyr Trp Gly Gln Gly Thr Pro Val Thr Val Ser Ser
            115                 120                 125

(2) INFORMATION FOR SEQ ID NO: 8:

(i) SEQUENCE CHARACTERISTICS:
        (A) LENGTH: 119 amino acids
```

(B) TYPE: amino acid
(C) STRANDEDNESS: <Unknown>
(D) TOPOLOGY: linear (ii) MOLECULE TYPE: protein (xi) SEQUENCE DESCRIPTION: SEQ ID NO: 8:

```
Gln Val Gln Leu Gln Glu Ser Gly Pro Gly Leu Val Arg Pro Ser Gln
1               5                   10                  15

Thr Leu Ser Leu Thr Cys Thr Ala Ser Gly Phe Asp Phe Thr Thr Tyr
            20                  25                  30

Trp Met Ser Trp Val Arg Gln Pro Pro Gly Arg Gly Leu Glu Trp Ile
            35                  40                  45

Gly Glu Ile His Pro Asp Ser Ser Thr Ile Asn Tyr Ala Pro Ser Leu
        50                  55                  60

Lys Asp Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Ser Leu Tyr Phe Gly Phe Pro Trp Phe Ala Tyr Trp Gly Gln Gly
            100                 105                 110

Thr Thr Val Thr Val Ser Ser
        115
```

(2) INFORMATION FOR SEQ ID NO: 9:

(i) SEQUENCE CHARACTERISTICS:
(A) LENGTH: 119 amino acids
(B) TYPE: amino acid
(C) STRANDEDNESS: <Unknown>
(D) TOPOLOGY: linear (ii) MOLECULE TYPE: protein (xi) SEQUENCE DESCRIPTION: SEQ ID NO: 9:

```
Gln Val Gln Leu Gln Glu Ser Gly Pro Gly Leu Val Arg Pro Ser Gln
1               5                   10                  15

Thr Leu Ser Leu Thr Cys Thr Ala Ser Gly Phe Asp Phe Thr Thr Tyr
            20                  25                  30

Trp Met Ser Trp Val Arg Gln Pro Pro Gly Arg Gly Leu Glu Trp Ile
            35                  40                  45

Gly Glu Ile His Pro Asp Ser Ser Thr Ile Asn Tyr Ala Pro Ser Leu
        50                  55                  60

Lys Asp Arg Val Thr Met Leu Arg Asp Thr Ser Lys Asn Thr Leu Tyr
65                  70                  75                  80

Leu Arg Leu Ser Ser Val Thr Ala Ala Asp Thr Ala Val Tyr Tyr Cys
                85                  90                  95

Ala Ser Leu Tyr Phe Gly Phe Pro Trp Phe Ala Tyr Trp Gly Gln Gly
            100                 105                 110

Thr Thr Val Thr Val Ser Ser
        115
```

(2) INFORMATION FOR SEQ ID NO: 10:

(i) SEQUENCE CHARACTERISTICS:
(A) LENGTH: 119 amino acids
(B) TYPE: amino acid
(C) STRANDEDNESS: <Unknown>
(D) TOPOLOGY: linear (ii) MOLECULE TYPE: protein (xi) SEQUENCE DESCRIPTION: SEQ ID NO: 10:

| Gln | Val | Gln | Leu | Gln | Glu | Ser | Gly | Pro | Gly | Leu | Val | Arg | Pro | Ser | Gln |
| 1 | | | | 5 | | | | | 10 | | | | | 15 | |

| Thr | Leu | Ser | Leu | Thr | Cys | Thr | Ala | Ser | Gly | Phe | Asp | Phe | Thr | Thr | Tyr |
| | | | 20 | | | | | 25 | | | | | 30 | | |

| Trp | Met | Ser | Trp | Val | Arg | Gln | Pro | Pro | Gly | Arg | Gly | Leu | Glu | Trp | Ile |
| | | 35 | | | | | 40 | | | | | 45 | | | |

| Gly | Glu | Ile | His | Pro | Asp | Ser | Ser | Thr | Ile | Asn | Tyr | Ala | Pro | Ser | Leu |
| | 50 | | | | | 55 | | | | | 60 | | | | |

| Lys | Asp | Arg | Val | Thr | Met | Leu | Arg | Asp | Thr | Ser | Lys | Asn | Gln | Phe | Ser |
| 65 | | | | | 70 | | | | | 75 | | | | | 80 |

| Leu | Arg | Leu | Ser | Lys | Val | Arg | Ser | Glu | Asp | Thr | Ala | Val | Tyr | Tyr | Cys |
| | | | | 85 | | | | | 90 | | | | | 95 | |

| Ala | Ser | Leu | Tyr | Phe | Gly | Phe | Pro | Trp | Phe | Ala | Tyr | Trp | Gly | Gln | Gly |
| | | | 100 | | | | | 105 | | | | | 110 | | |

| Thr | Thr | Val | Thr | Val | Ser | Ser |
| | | | 115 | | | |

(2) INFORMATION FOR SEQ ID NO: 11:

(i) SEQUENCE CHARACTERISTICS:
        (A) LENGTH: 119 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 11:

| Gln | Val | Gln | Leu | Gln | Glu | Ser | Gly | Pro | Gly | Leu | Val | Arg | Pro | Ser | Gln |
| 1 | | | | 5 | | | | | 10 | | | | | 15 | |

| Thr | Leu | Ser | Leu | Thr | Cys | Thr | Ala | Ser | Gly | Phe | Asp | Phe | Thr | Thr | Tyr |
| | | | 20 | | | | | 25 | | | | | 30 | | |

| Trp | Met | Ser | Trp | Val | Arg | Gln | Pro | Pro | Gly | Arg | Gly | Leu | Glu | Trp | Ile |
| | | 35 | | | | | 40 | | | | | 45 | | | |

| Gly | Glu | Ile | His | Pro | Asp | Ser | Ser | Thr | Ile | Asn | Tyr | Ala | Pro | Ser | Leu |
| | 50 | | | | | 55 | | | | | 60 | | | | |

| Lys | Asp | Lys | Phe | Ile | Val | Ser | Arg | Asp | Thr | Ser | Lys | Asn | Gln | Phe | Ser |
| 65 | | | | | 70 | | | | | 75 | | | | | 80 |

| Leu | Arg | Leu | Ser | Ser | Val | Thr | Ala | Ala | Asp | Thr | Ala | Val | Tyr | Tyr | Cys |
| | | | | 85 | | | | | 90 | | | | | 95 | |

| Ala | Ser | Leu | Tyr | Phe | Gly | Phe | Pro | Trp | Phe | Ala | Tyr | Trp | Gly | Gln | Gly |
| | | | 100 | | | | | 105 | | | | | 110 | | |

| Thr | Thr | Val | Thr | Val | Ser | Ser |
| | | | 115 | | | |

(2) INFORMATION FOR SEQ ID NO: 12:

(i) SEQUENCE CHARACTERISTICS:
        (A) LENGTH: 119 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 12:

| Glu | Val | Gln | Leu | Val | Glu | Ser | Gly | Gly | Gly | Val | Val | Gln | Pro | Gly | Arg |
| 1 | | | | 5 | | | | | 10 | | | | | 15 | |

```
Ser Leu Arg Leu Ser Cys Ser Ser Ser Gly Phe Asp Phe Thr Thr Tyr
            20                  25                  30

Trp Met Ser Trp Val Arg Gln Ala Pro Gly Lys Gly Leu Glu Trp Val
        35                  40                  45

Ala Glu Ile His Pro Asp Ser Ser Thr Ile Asn Tyr Ala Pro Ser Leu
    50                  55                  60

Lys Asp Arg Phe Thr Ile Ser Arg Asp Asn Ser Lys Asn Thr Leu Phe
 65                  70                  75                  80

Leu Gln Met Asp Ser Leu Arg Pro Glu Asp Thr Gly Val Tyr Phe Cys
                85                  90                  95

Ala Ser Leu Tyr Phe Gly Phe Pro Trp Phe Ala Tyr Trp Gly Gln Gly
                100                 105                 110

Thr Pro Val Thr Val Ser Ser
            115
```

(2) INFORMATION FOR SEQ ID NO: 13:

(i) SEQUENCE CHARACTERISTICS:
        (A) LENGTH: 119 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 13:

```
Glu Val Gln Leu Val Glu Ser Gly Gly Gly Val Val Gln Pro Gly Arg
 1               5                   10                  15

Ser Leu Arg Leu Ser Cys Ser Ala Ser Gly Phe Asp Phe Thr Thr Tyr
            20                  25                  30

Trp Met Ser Trp Val Arg Gln Ala Pro Gly Lys Gly Leu Glu Trp Ile
        35                  40                  45

Gly Glu Ile His Pro Asp Ser Ser Thr Ile Asn Tyr Ala Pro Ser Leu
    50                  55                  60

Lys Asp Arg Phe Thr Ile Ser Arg Asp Asn Ser Lys Asn Thr Leu Phe
 65                  70                  75                  80

Leu Gln Met Asp Ser Leu Arg Pro Glu Asp Thr Gly Val Tyr Phe Cys
                85                  90                  95

Ala Ser Leu Tyr Phe Gly Phe Pro Trp Phe Ala Tyr Trp Gly Gln Gly
                100                 105                 110

Thr Pro Val Thr Val Ser Ser
            115
```

(2) INFORMATION FOR SEQ ID NO: 14:

(i) SEQUENCE CHARACTERISTICS:
        (A) LENGTH: 119 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 14:

```
Glu Val Gln Leu Val Glu Ser Gly Gly Gly Val Val Gln Pro Gly Arg
 1               5                   10                  15

Ser Leu Arg Leu Ser Cys Ser Ala Ser Gly Phe Asp Phe Thr Thr Tyr
            20                  25                  30

Trp Met Ser Trp Val Arg Gln Ala Pro Gly Lys Gly Leu Glu Trp Ile
```

```
                  35                  40                  45
Gly Glu Ile His Pro Asp Ser Ser Thr Ile Asn Tyr Ala Pro Ser Leu
     50                  55                  60

Lys Asp Arg Phe Thr Ile Ser Arg Asp Asn Ala Lys Asn Thr Leu Phe
65                   70                  75                  80

Leu Gln Met Asp Ser Leu Arg Pro Glu Asp Thr Gly Val Tyr Phe Cys
                 85                  90                  95

Ala Ser Leu Tyr Phe Gly Phe Pro Trp Phe Ala Tyr Trp Gly Gln Gly
                100                 105                 110

Thr Pro Val Thr Val Ser Ser
            115
```

(2) INFORMATION FOR SEQ ID NO: 15:

(i) SEQUENCE CHARACTERISTICS:
        (A) LENGTH: 119 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 15:

```
Glu Val Gln Leu Val Glu Ser Gly Gly Gly Val Val Gln Pro Gly Arg
1               5                  10                  15

Ser Leu Arg Leu Ser Cys Ser Ala Ser Gly Phe Asp Phe Thr Thr Tyr
             20                  25                  30

Trp Met Ser Trp Val Arg Gln Ala Pro Gly Lys Gly Leu Glu Trp Ile
             35                  40                  45

Gly Glu Ile His Pro Asp Ser Ser Thr Ile Asn Tyr Ala Pro Ser Leu
     50                  55                  60

Lys Asp Arg Phe Thr Ile Ser Arg Asp Asn Ala Lys Asn Thr Leu Tyr
65                   70                  75                  80

Leu Gln Met Asp Ser Leu Arg Pro Glu Asp Thr Gly Val Tyr Phe Cys
                 85                  90                  95

Ala Ser Leu Tyr Phe Gly Phe Pro Trp Phe Ala Tyr Trp Gly Gln Gly
                100                 105                 110

Thr Pro Val Thr Val Ser Ser
            115
```

(2) INFORMATION FOR SEQ ID NO: 16:

(i) SEQUENCE CHARACTERISTICS:
        (A) LENGTH: 357 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..357

(xi) SEQUENCE DESCRIPTION: SEQ ID NO: 16:

```
GAG GTC CAA CTG GTG GAG AGC GGT GGA GGT GTT GTG CAA CCT GGC CGG        48
Glu Val Gln Leu Val Glu Ser Gly Gly Gly Val Val Gln Pro Gly Arg
             110                 115                 120

TCC CTG CGC CTG TCC TGC TCC TCG TCT GGC TTC GAT TTC ACC ACA TAT        96
Ser Leu Arg Leu Ser Cys Ser Ser Ser Gly Phe Asp Phe Thr Thr Tyr
             125                 130                 135
```

```
TGG ATG AGT TGG GTG AGA CAG GCA CCT GGA AAA GGT CTT GAG TGG GTT      144
Trp Met Ser Trp Val Arg Gln Ala Pro Gly Lys Gly Leu Glu Trp Val
    140                 145                 150

GCA GAA ATT CAT CCA GAT AGC AGT ACG ATT AAC TAT GCG CCG TCT CTA      192
Ala Glu Ile His Pro Asp Ser Ser Thr Ile Asn Tyr Ala Pro Ser Leu
155                 160                 165                 170

AAG GAT AGA TTT ACA ATA TCG CGA GAC AAC AGC AAG AAC ACA TTG TTC      240
Lys Asp Arg Phe Thr Ile Ser Arg Asp Asn Ser Lys Asn Thr Leu Phe
                175                 180                 185

CTG CAA ATG GAC AGC CTG AGA CCC GAA GAC ACC GGG GTC TAT TTT TGT      288
Leu Gln Met Asp Ser Leu Arg Pro Glu Asp Thr Gly Val Tyr Phe Cys
            190                 195                 200

GCA AGC CTT TAC TTC GGC TTC CCC TGG TTT GCT TAT TGG GGC CAA GGG      336
Ala Ser Leu Tyr Phe Gly Phe Pro Trp Phe Ala Tyr Trp Gly Gln Gly
        205                 210                 215

ACC CCG GTC ACC GTC TCC TCA                                          357
Thr Pro Val Thr Val Ser Ser
220                 225

(2) INFORMATION FOR SEQ ID NO: 17:

(i) SEQUENCE CHARACTERISTICS:
        (A) LENGTH: 119 amino acids
        (B) TYPE: amino acid
        (D) TOPOLOGY: linear (ii) MOLECULE TYPE: protein (xi) SEQUENCE DESCRIPTION: SEQ ID NO: 17:

Glu Val Gln Leu Val Glu Ser Gly Gly Gly Val Val Gln Pro Gly Arg
 1               5                  10                  15

Ser Leu Arg Leu Ser Cys Ser Ser Gly Phe Asp Phe Thr Thr Tyr
            20                  25                  30

Trp Met Ser Trp Val Arg Gln Ala Pro Gly Lys Gly Leu Glu Trp Val
        35                  40                  45

Ala Glu Ile His Pro Asp Ser Ser Thr Ile Asn Tyr Ala Pro Ser Leu
    50                  55                  60

Lys Asp Arg Phe Thr Ile Ser Arg Asp Asn Ser Lys Asn Thr Leu Phe
65                  70                  75                  80

Leu Gln Met Asp Ser Leu Arg Pro Glu Asp Thr Gly Val Tyr Phe Cys
                85                  90                  95

Ala Ser Leu Tyr Phe Gly Phe Pro Trp Phe Ala Tyr Trp Gly Gln Gly
            100                 105                 110

Thr Pro Val Thr Val Ser Ser
        115

(2) INFORMATION FOR SEQ ID NO: 18:

(i) SEQUENCE CHARACTERISTICS:
        (A) LENGTH: 318 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..318

(xi) SEQUENCE DESCRIPTION: SEQ ID NO: 18:

GAC ATC CAG CTG ACC CAG AGC CCA AGC AGC CTG AGC GCC AGC GTG GGT       48
Asp Ile Gln Leu Thr Gln Ser Pro Ser Ser Leu Ser Ala Ser Val Gly
```

```
                120                 125                 130                 135
GAC AGA GTG ACC ATC ACC TGT AAG GCC AGT CAG GAT GTG GGT ACT TCT          96
Asp Arg Val Thr Ile Thr Cys Lys Ala Ser Gln Asp Val Gly Thr Ser
                140                 145                 150

GTA GCT TGG TAC CAG CAG AAG CCA GGT AAG GCT CCA AAG CTG CTG ATC          144
Val Ala Trp Tyr Gln Gln Lys Pro Gly Lys Ala Pro Lys Leu Leu Ile
                155                 160                 165

TAC TGG ACA TCC ACC CGG CAC ACT GGT GTG CCA AGC AGA TTC AGC GGT          192
Tyr Trp Thr Ser Thr Arg His Thr Gly Val Pro Ser Arg Phe Ser Gly
                170                 175                 180

AGC GGT AGC GGT ACC GAC TTC ACC TTC ACC ATC AGC AGC CTC CAG CCA          240
Ser Gly Ser Gly Thr Asp Phe Thr Phe Thr Ile Ser Ser Leu Gln Pro
                185                 190                 195

GAG GAC ATC GCC ACC TAC TAC TGC CAG CAA TAT AGC CTC TAT CGG TCG          288
Glu Asp Ile Ala Thr Tyr Tyr Cys Gln Gln Tyr Ser Leu Tyr Arg Ser
200                 205                 210                 215

TTC GGC CAA GGG ACC AAG GTG GAA ATC AAA                                  318
Phe Gly Gln Gly Thr Lys Val Glu Ile Lys
                220                 225

(2) INFORMATION FOR SEQ ID NO: 19:

(i) SEQUENCE CHARACTERISTICS:
        (A) LENGTH: 106 amino acids
        (B) TYPE: amino acid
        (D) TOPOLOGY: linear (ii) MOLECULE TYPE: protein (xi) SEQUENCE DESCRIPTION: SEQ ID NO: 19:

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ser
                20                  25                  30

Val Ala Trp Tyr Gln Gln Lys Pro Gly Lys Ala Pro Lys Leu Leu Ile
            35                  40                  45

Tyr Trp Thr Ser Thr Arg His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Ser Leu Tyr Arg Ser
                85                  90                  95

Phe Gly Gln Gly Thr Lys Val Glu Ile Lys
                100                 105

(2) INFORMATION FOR SEQ ID NO: 20:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 20:

Lys Ala Ser Gln Asp Val Gly Thr Ser Val Ala
1               5                   10

(2) INFORMATION FOR SEQ ID NO: 21:

(i) SEQUENCE CHARACTERISTICS:
```

(A) LENGTH: 7 amino acids
            (B) TYPE: amino acid
            (C) STRANDEDNESS: <Unknown>
            (D) TOPOLOGY: linear (ii) MOLECULE TYPE: protein (xi) SEQUENCE DESCRIPTION: SEQ ID NO: 21:

Trp Thr Ser Thr Arg His Thr
1               5

(2) INFORMATION FOR SEQ ID NO: 22:

(i) SEQUENCE CHARACTERISTICS:
            (A) LENGTH: 8 amino acids
            (B) TYPE: amino acid
            (C) STRANDEDNESS: <Unknown>
            (D) TOPOLOGY: linear (ii) MOLECULE TYPE: protein (xi) SEQUENCE DESCRIPTION: SEQ ID NO: 22:

Gln Gln Tyr Ser Leu Tyr Arg Ser
1               5

(2) INFORMATION FOR SEQ ID NO: 23:

(i) SEQUENCE CHARACTERISTICS:
            (A) LENGTH: 5 amino acids
            (B) TYPE: amino acid
            (C) STRANDEDNESS: <Unknown>
            (D) TOPOLOGY: linear (ii) MOLECULE TYPE: protein (xi) SEQUENCE DESCRIPTION: SEQ ID NO: 23:

Thr Tyr Trp Met Ser
1               5

(2) INFORMATION FOR SEQ ID NO: 24:

(i) SEQUENCE CHARACTERISTICS:
            (A) LENGTH: 17 amino acids
            (B) TYPE: amino acid
            (C) STRANDEDNESS: <Unknown>
            (D) TOPOLOGY: linear (ii) MOLECULE TYPE: protein (xi) SEQUENCE DESCRIPTION: SEQ ID NO: 24:

Glu Ile His Pro Asp Ser Ser Thr Ile Asn Tyr Ala Pro Ser Leu Lys
1               5                   10                  15

Asp (2) INFORMATION FOR SEQ ID NO: 25:

(i) SEQUENCE CHARACTERISTICS:
            (A) LENGTH: 10 amino acids
            (B) TYPE: amino acid
            (C) STRANDEDNESS: <Unknown>
            (D) TOPOLOGY: linear (ii) MOLECULE TYPE: protein (xi) SEQUENCE DESCRIPTION: SEQ ID NO: 25:

Leu Tyr Phe Gly Phe Pro Trp Phe Ala Tyr
1               5                   10

(2) INFORMATION FOR SEQ ID NO: 26:

(i) SEQUENCE CHARACTERISTICS:
        (A) LENGTH: 23 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 26:

```
Asp Ile Gln Leu Thr Gln Ser Pro Ser Ser Leu Ser Ala Ser Val Gly
1               5                   10                  15

Asp Arg Val Thr Ile Thr Cys
            20
```

(2) INFORMATION FOR SEQ ID NO: 27:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 27:

```
Trp Tyr Gln Gln Lys Pro Gly Lys Ala Pro Lys Leu Leu Ile Tyr
1               5                   10                  15
```

(2) INFORMATION FOR SEQ ID NO: 28:

(i) SEQUENCE CHARACTERISTICS:
        (A) LENGTH: 32 amino acids
        (B) TYPE: amino acid
        (C) STRANDEDNESS: <Unknown>
        (D) TOPOLOGY: linear (ii) MOLECULE TYPE: protein (ix) FEATURE:
        (A) NAME/KEY: Modified-site
        (B) LOCATION: 4
        (D) OTHER INFORMATION: /note= "At site 4, Xaa = Ser or
            Asp."

(ix) FEATURE:
        (A) NAME/KEY: Modified-site
        (B) LOCATION: 10
        (D) OTHER INFORMATION: /note= "At site 10, Xaa = Gly or
            Val."

(xi) SEQUENCE DESCRIPTION: SEQ ID NO: 28:

```
Gly Val Pro Xaa Arg Phe Ser Gly Ser Xaa Ser Gly Thr Asp Phe Thr
1               5                   10                  15

Phe Thr Ile Ser Ser Leu Gln Pro Glu Asp Ile Ala Thr Tyr Tyr Cys
            20                  25                  30
```

(2) INFORMATION FOR SEQ ID NO: 29:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 29:

Phe Gly Gln Gly Thr Lys Val Glu Ile Lys

```
1               5                   10
```

(2) INFORMATION FOR SEQ ID NO: 30:

(i) SEQUENCE CHARACTERISTICS:
        (A) LENGTH: 30 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 30:

```
Glu Val Gln Leu Val Glu Ser Gly Gly Gly Val Val Gln Pro Gly Arg
1               5                   10                  15
Ser Leu Arg Leu Ser Cys Ser Ser Ser Gly Phe Asp Phe Thr
            20                  25                  30
```

(2) INFORMATION FOR SEQ ID NO: 31:

(i) SEQUENCE CHARACTERISTICS:
        (A) LENGTH: 30 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 31:

```
Glu Val Gln Leu Val Glu Ser Gly Gly Gly Val Val Gln Pro Gly Arg
1               5                   10                  15
Ser Leu Arg Leu Ser Cys Ser Ala Ser Gly Phe Asp Phe Thr
            20                  25                  30
```

(2) INFORMATION FOR SEQ ID NO: 32:

(i) SEQUENCE CHARACTERISTICS:
        (A) LENGTH: 30 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 32:

```
Gln Val Gln Leu Gln Glu Ser Gly Pro Gly Leu Val Arg Pro Ser Gln
1               5                   10                  15
Thr Leu Ser Leu Thr Cys Thr Ser Ser Gly Phe Asp Phe Thr
            20                  25                  30
```

(2) INFORMATION FOR SEQ ID NO: 33:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 33:

```
Trp Val Arg Gln Ala Pro Gly Lys Gly Leu Glu Trp Val Ala
1               5                   10
```

(2) INFORMATION FOR SEQ ID NO: 34:

(i) SEQUENCE CHARACTERISTICS:

(A) LENGTH: 14 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 34:

Trp Val Arg Gln Ala Pro Gly Lys Gly Leu Glu Trp Ile Ala
1               5                  10

(2) INFORMATION FOR SEQ ID NO: 35:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 35:

Trp Val Arg Gln Pro Pro Gly Lys Gly Leu Glu Trp Ile Ala
1               5                  10

(2) INFORMATION FOR SEQ ID NO: 36:

(i) SEQUENCE CHARACTERISTICS:
        (A) LENGTH: 32 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 36:

Arg Phe Thr Ile Ser Arg Asp Asn Ser Lys Asn Thr Leu Phe Leu Gln
1               5                  10                  15

Met Asp Ser Leu Arg Pro Glu Asp Thr Gly Val Tyr Phe Cys Ala Ser
                20                  25                  30

(2) INFORMATION FOR SEQ ID NO: 37:

(i) SEQUENCE CHARACTERISTICS:
        (A) LENGTH: 32 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 37:

Arg Phe Thr Ile Ser Arg Asp Asn Ala Lys Asn Thr Leu Phe Leu Gln
1               5                  10                  15

Met Asp Ser Leu Arg Pro Glu Asp Thr Gly Val Tyr Phe Cys Ala Ser
                20                  25                  30

(2) INFORMATION FOR SEQ ID NO: 38:

(i) SEQUENCE CHARACTERISTICS:
        (A) LENGTH: 32 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 38:

```
Arg Val Thr Met Leu Arg Asp Thr Ser Lys Asn Gly Ser Phe Leu Arg
1               5                   10                  15

Leu Ser Ser Val Thr Ala Ala Asp Thr Ala Val Tyr Tyr Cys Ala Ser
            20              25                  30
```

(2) INFORMATION FOR SEQ ID NO: 39:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 39:

```
Trp Gly Gln Gly Thr Pro Val Thr Val Ser Ser
1               5                   10
```

(2) INFORMATION FOR SEQ ID NO: 40:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 40:

```
Trp Gly Gln Gly Thr Thr Val Thr Val Ser Ser
1               5                   10
```

(2) INFORMATION FOR SEQ ID NO: 41:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 41:

GGAAGCTTAG ACAGATGGGG GTGTCGTTTT G                      31

(2) INFORMATION FOR SEQ ID NO: 42:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 42:

TGAGGAGACG GTGACCGTGG TCCCTTGGCC CCAG                34

(2) INFORMATION FOR SEQ ID NO: 43:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 43:

AGGTSMARCT GCAGSAGTCW GG                                              22

(2) INFORMATION FOR SEQ ID NO: 44:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 44:

TGGAATTCAT GGRATGGAGC TGGRTCWTBH TCTT                                 34

(2) INFORMATION FOR SEQ ID NO: 45:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 45:

TGGAATTCAT GRACTTCDGG YTCAACTKRR TTT                                  33

(2) INFORMATION FOR SEQ ID NO: 46:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 46:

GGAAGCTTGA AGATGGATAC AGTTGGTGCA GC                                   32

(2) INFORMATION FOR SEQ ID NO: 47:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 47:

GTTAGATCTC CAGCTTGGTC CC                                              22

(2) INFORMATION FOR SEQ ID NO: 48:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 48:

GTTAGATCTC CAGTTTGGTG CCT                                             23

(2) INFORMATION FOR SEQ ID NO: 49:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 49:

GACATTCAGC TGACCCAGTC TCCA                        24

(2) INFORMATION FOR SEQ ID NO: 50:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 50:

GACRTTCAGC TGACCCAGGM TGMA                        24

(2) INFORMATION FOR SEQ ID NO: 51:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 51:

GACATTCAGC TGACCCA                              17

(2) INFORMATION FOR SEQ ID NO: 52:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 52:

GACATTGAGC TCACCCAGTC TCCA                        24

(2) INFORMATION FOR SEQ ID NO: 53:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 53:

TTGAATTCGG TGCCAGAKCW SAHATYGTKA TG                32

(2) INFORMATION FOR SEQ ID NO: 54:

(i) SEQUENCE CHARACTERISTICS:

(A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 54:

TTGAATTCGG TGCCAGAKCW SAHATYGTKC TC                        32

(2) INFORMATION FOR SEQ ID NO: 55:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 55:

TTGAATTCGG AGCTGATGGG AACATTGTAA TG                        32

(2) INFORMATION FOR SEQ ID NO: 56:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 56:

CWGAGAAATT CAGCTGACCC AGTCTC                               26

(2) INFORMATION FOR SEQ ID NO: 57:

(i) SEQUENCE CHARACTERISTICS:
        (A) LENGTH: 119 amino acids
        (B) TYPE: amino acid
        (C) STRANDEDNESS: single
        (D) TOPOLOGY: linear (xi) SEQUENCE DESCRIPTION: SEQ ID NO: 57:

Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Thr Tyr
            20                  25                  30

Trp Met Ser Trp Val Arg Gln Pro Pro Gly Arg Gly Leu Glu Trp Ile
        35                  40                  45

Gly Glu Ile His Pro Asp Ser Ser Thr Ile Asn Tyr Ala Pro Ser Leu
    50                  55                  60

Lys Asp Arg Val Thr Met Leu Val Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Leu Tyr Phe Gly Phe Pro Trp Phe Ala Tyr Trp Gly Gln Gly
            100                 105                 110

Thr Thr Val Thr Val Ser Ser
        115

(2) INFORMATION FOR SEQ ID NO: 58:

-continued

```
    (i) SEQUENCE CHARACTERISTICS:
        (A) LENGTH: 119 amino acids
        (B) TYPE: amino acid
        (C) STRANDEDNESS: single
        (D) TOPOLOGY: linear (xi) SEQUENCE DESCRIPTION: SEQ ID NO: 58:

Glu Val Gln Leu Val Glu Ser Gly Gly Gly Val Val Gln Pro Gly Arg
1               5                  10                  15

Ser Leu Arg Leu Ser Cys Ser Ser Ser Gly Phe Ile Phe Ser Thr Tyr
            20                  25                  30

Trp Met Ser Trp Val Arg Gln Ala Pro Gly Lys Gly Leu Glu Trp Val
        35                  40                  45

Ala Glu Ile His Pro Asp Ser Ser Thr Ile Asn Tyr Ala Pro Ser Leu
    50                  55                  60

Lys Asp Arg Phe Thr Ile Ser Arg Asp Asn Ser Lys Asn Thr Leu Phe
65                  70                  75                  80

Leu Gln Met Asp Ser Leu Arg Pro Lys Asp Thr Gly Val Tyr Phe Cys
                85                  90                  95

Ala Arg Leu Tyr Phe Gly Phe Pro Trp Phe Ala Tyr Trp Gly Gln Gly
            100                 105                 110

Thr Pro Val Thr Val Ser Ser
            115
```

CDR-GRAFTED TYPE III ANTI-CEA HUMANIZED MOUSE MONOCLONAL ANTIBODIES

This application is a divisional of application Ser. No. 08/318,157, filed Oct. 5, 1994 now U.S. Pat. No. 5,874,540.

BACKGROUND OF THE INVENTION

The invention relates to immunological reagents for diagnostic and therapeutic use in colon and other cancers. In particular, the invention relates to humanized anti-carcinoembryonic antigen ("CEA") monoclonal antibodies ("mAbs") that have the binding affinity characteristics of corresponding mouse anti-CEA mAb (MN14) and the antigenic and effector properties of a human antibody. Further, the invention relates to humanized mAbs in which the complementarity determining regions ("CDRs") of an anti-CEA murine mAb is grafted into the framework regions of a human antibody, to DNAs that encode such CDR-grafted antibodies, to vectors and transformed hosts for propagating and expressing the DNAs, and to conjugates of the antibodies useful in diagnostic and therapeutic applications.

A promising approach to cancer diagnosis and therapy involves the use of targeting antibodies to deliver diagnostic and therapeutic agents directly to the site of a malignancy. Over the past decade, a wide variety of tumor-specific antibodies and antibody fragments have been developed, as have methods to conjugate the antibodies to drugs, toxins, radionuclides or other agents, and to administer the conjugates to patients. These efforts have produced great progress, but a variety of largely unanticipated problems have limited the diagnostic and therapeutic utility of some of the reagents thus far developed.

Among the most intractable problems is that which is caused by the human immune system itself, which may respond to the targeting conjugate as a foreign antigen. For instance, patients treated with drugs or radionuclides complexed with murine monoclonal antibodies (which have been the most commonly used targeting antibodies for human) develop circulating human anti-mouse antibodies (HAMAs) and a generalized immediate type-III hypersensitivity reaction to the antibody moiety of the conjugate. Furthermore, even when adverse side effects are minimal (for example, as in a single administration), circulating HAMAs decrease the effective concentration of the targeting agent in the patient and therefore limiting the diagnostic or therapeutic agent from reaching the target site.

Several approaches have been developed to overcome or avoid this problem, with only limited success. One strategy has been to chemically modify the targeting antibody to suppress its antigenicity. For example, conjugation of polyethylene glycol to the targeting antibody (PEGylation) is reported to reduce antigenicity of antibodies. Another approach has been to characterize the situs of antigenicity in an antibody and then remove it. In this vein, Fab', F(ab)$_2$ and other antibody fragments have been used in place of whole IgG. In addition, attempts have been made to reduce the adverse effects of HAMA by plasmaphoretically removing HAMA from blood. Immunosuppressive techniques also have been used to ameliorate the adverse effect of the foreign antibody sufficiently to permit multiple treatments with the targeting agent.

None of these approaches has proven altogether satisfactory. An important need persists for a means to reduce or eliminate the adverse immune response to targeting antibody and antibody conjugates in order to gain the full benefit of these diagnostic and therapeutic agents.

This goal has been achieved with the CDR-grafted humanized murine anti-human CEA mAbs that are described below.

SUMMARY OF THE INVENTION

It is an object of the present invention to provide a humanized Class III anti-CEA mAb in which the CDRs of a murine Class III anti-CEA mAb (MN14) are functionally engrafted to the amino acid sequence of a human antibody or antibody fragment to provide an immunological reagent with the anti-CEA binding properties of the murine Class III, anti-CEA mAb and the immunogenic properties of a human mAb in a human patient.

It is another object of the present invention to provide DNA constructs encoding such antibodies. Particular objects in this regard are substrate DNAs that facilitate genetic manipulation to produce improved antibodies and DNAs encoding the antibodies with advantageous properties in cell culture and antibody production.

Yet another object of the invention is to provide vectors for propagating the DNA and for expressing the antibody. A related object of the invention is to provide cells containing a vector for the purposes of storage, propagation, antibody production and therapeutic applications.

Still another object of the invention is to provide compositions comprising the antibodies for use in diagnosis and therapy. In this regard it is an object of the invention to provide conjugates comprising the antibodies complexed with imaging agents and therapeutic agents for ex vivo and in vivo imaging, diagnosis, prognosis and therapy, among others.

In accomplishing the foregoing objects, there has been provided, in accordance with one aspect of the present invention, a humanized mouse mAb, comprising the CDRs of a murine Class III, anti-CEA mAb (MN-14) engrafted to the framework regions of a heterologous (human) antibody, wherein the thus humanized mAb antibody retains the Class III, anti-CEA binding specificity of the murine mAb but in the patient is less immunogenic than is the parent MN-14 murine monoclonal antibody.

In a highly preferred embodiment, the light chain variable regions of the humanized antibody are characterized by the formula:

wherein each FR is separately a framework region of a human antibody, and each CDR is separately in a complementarity-determining region of the light chains of MN-14, and the subscripts refer to light ("L") chain regions. The heavy chain variable regions are characterized by the formula:

wherein FR and CDR have the same meanings as above, and wherein the subscripts "H" refer to heavy chain regions.

In one embodiment, $CDR_{L1}$ has the amino acid sequence KASQD VGTSVA (SEQ. ID NO. 20); $CDR_{L2}$ has the amino acid sequence WTSTR HT (SEQ. ID NO. 21); $CDR_{L3}$ has the amino acid sequence QQYSL YRS (SEQ. ID NO. 22); $CDR_{H1}$ has the amino acid sequence TYWMS (SEQ. ID. NO. 23); $CDR_{H2}$ has the amino acid sequence EIHP DSSTI NYAPS LKD (SEQ. ID NO. 24); and, $CDR_{H3}$ has the amino acid sequence LYFGF PWFAY (SEQ. ID NO. 25).

In another embodiment, FRL, has the amino acid sequence DIQLT QSPSS LSASV GDRVT ITC (SEQ. ID NO. 26); FR$_{L2}$ has the amino acid sequence WYQQK PGKAP KLLIY (SEQ. ID NO. 27); FR$_{L3}$ has the amino acid sequence GVP(S or D)RF SGS(G or V)S GTDFT FTISS LQPED IATYY C (SEQ. ID NO. 28); FR$_{L4}$ has the amino acid sequence FGQGT KVEIK (SEQ. ID NO. 29); FR$_{H1}$ has the amino acid sequence EVQLV ESGGG VVQPG RSLRL SCSSS GFDFT (SEQ. ID NO. 30), EVQLV ESGGG VVQPG RSLRL SCSAS GFDFT (SEQ. ID NO. 31), or QVQLQ ESGPG LVRPS QTLSL TCTSS GFDFT (SEQ. ID NO. 32); FR$_{H2}$ has the amino acid sequence WVRQA PGKGL EWVA (SEQ. ID NO. 33), WVRQA PGKGL EWIA (SEQ. ID NO. 34), or WVRQP PGRGL EWIA (SEQ. ID NO. 35); FR$_{H3}$ has the amino acid sequence RFTIS RDNSK NTLFL QMDSL RPEDT GVYFC AS (SEQ. ID NO. 36), RFTIS RDNAK NTLFL QMDSL RPEDT GVYFC AS (SEQ. ID NO. 37), or RVTML RDTSK NGSFL RLSSV TAADT AVYYC AS (SEQ. ID NO. 38); and FR$_{H4}$ has the amino acid sequence WGQGT PVIVS S (SEQ. ID NO. 39), or WGQGT TVTVS S (SEQ. ID NO. 40); and wherein C may be in the sulfhydryl or disulfide form.

Another preferred embodiment comprises a diagnostic or therapeutic agent complexed to Class III, anti-CEA humanized mAb in which the CDRs of the antibody are derived from those of the MN-14 murine mAb and the FRs are derived from those of the heterologous (human) antibody, wherein the conjugate retains the Class III, anti-CEA binding specificity of MN-14, but is in humans less immunogenic than is murine MN-14. In one such embodiment the light chain and heavy chain variable regions are characterized as shown above and have amino acid sequences also as described above.

In yet another preferred embodiment, a method for diagnosing or treating a patient comprises the step of administering in an appropriate regimen the conjugate of the previous preferred embodiment.

Another preferred embodiment comprises an isolated, purified DNA that encodes the light chain, the heavy chain or both chains of the humanized antibody described above.

Another preferred embodiment comprises the DNA sequence of the CDRs and FRs described above.

Other objects, features and advantages of the present invention will become apparent from the following detailed description and appended claims.

ILLUSTRATIVE GLOSSARY

The following terms or abbreviations are used in the present application. The meanings set out in this glossary are for illustrative purposes only. The full meaning of the terms will be apparent to those of skill in the art.

"CDR" is used as an abbreviation for Complementarity Determining Region. These are the regions within the variable regions of an antibody that are primarily, but not exclusively, responsible for antigen-antibody binding.

"FR" is an abbreviation for Framework Region. Broadly speaking, these are the portions of the variable regions of an antibody which lie adjacent to or flank the CDRs. In general, these regions have more of a structural function that affects the conformation of the variable region and are less directly responsible for the specific binding of antigen to antibody, although, nonetheless, the framework regions can affect the interaction.

"Chimeric" refers to an antibody in which the variable region is derived from a mouse antibody and the constant region is derived from an antibody from a heterologous (other) species.

"Humanized" refers to a chimeric antibody as defined above, but one in which the FR variable regions are derived from a human antibody.

"HAMA" refers to human antibodies directed to a mouse antibody, that are produced when a mouse antibody is administered to a human subject.

"HAHA" refers to human antibodies directed to a humanized mouse antibody.

"CEA" refers to carcinoembryonic antigen, a 180 kDa glycoprotein that is expressed in most adenocarcinomas of endodermally-derived digestive system epithelia and in some other cancers such as breast cancer and non-small cell lung cancer.

The letter "h" as a prefix means "humanized".

Other abbreviations are used in accordance with Roitt et al., IMMUNOLOGY, 3rd ed. Mosby Year Book Europe Ltd. (1993), the entirety of which is herein incorporated by reference.

These and other terms used in the present disclosure are used in the same sense as ordinarily they are employed in the arts to which this invention pertains.

BRIEF DESCRIPTION OF THE FIGURES

FIGS. 1A and 1B (SEQ. ID. NOS. 1 and 2) shows the consensus DNA sequence of murine NEWM MN-14 variable region heavy chain ("VH") and its protein translation product. The CDRs are enclosed in boxes.

FIGS. 2A and 2B (SEQ. ID. NOS. 3 and 4) shows the consensus DNA sequence of murine MN-14 variable region light chain ("VK") and its protein translation product. The CDRs are enclosed in boxes.

FIGS. 6A, 6B and 6C shows a comparison of the amino acid sequence between murine (SEQ. ID NO. 2) and humanized (SEQ. ID NOS. 57, 8–11, 58 and 12–15). MN-14 VH framework residues (FR). Only human FR residues different from the mouse are shown. CDAs for NEWM and KOL are also not shown. The position of the substitution is indicated according to the Kabat et al. numbering system. The 3 CDRs are boxed.

FIG. 8 shows the DNA sequence and corresponding amino acid sequence (SEQ. ID NOS. 18 and 19) of the MN-14HuVK region. CDRs are boxed.

DETAILED DESCRIPTION OF THE INVENTION

Figure 3:
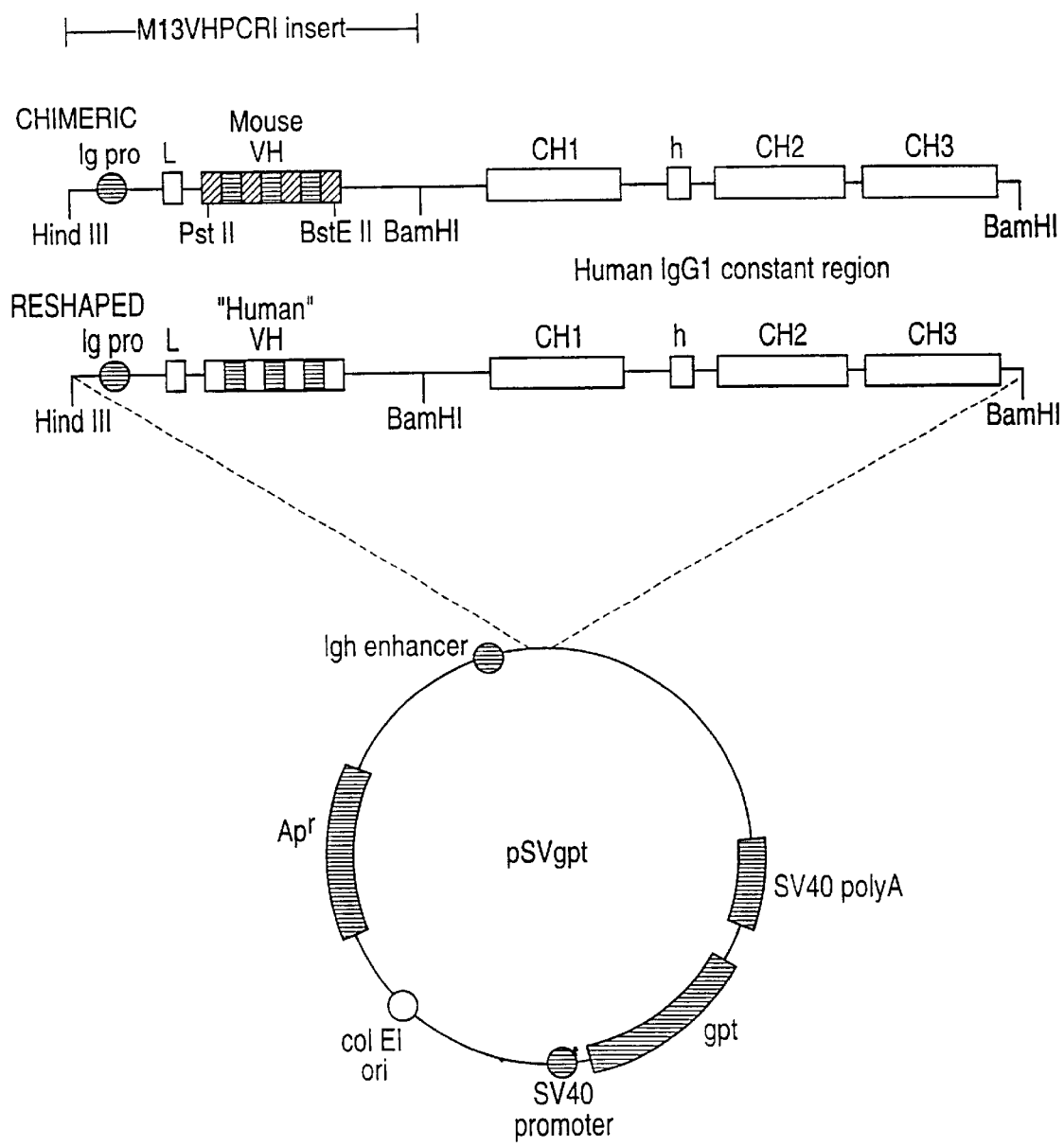
FIG. 3 shows a vector for the expression of chimeric or humanized MN-14 heavy chain gene. The schematic diagram shows both the chimeric and a reshaped heavy chain immunoglobulin (Ig) gene and the pSVgpt expression vector. The diagram at top, labeled "CHIMERIC," is a map showing DNA encoding the MN-14 mouse VH region joined to DNA encoding a human IgG1 constant region. In the MN-14 VH region the three CDRs are indicated by the three dark areas. The FRs are indicated by the four stippled areas. The middle diagram, labeled "RESHAPED" shows the humanization of the MN-14 VH region in which the mouse FRs have been replaced by human FRs, indicated by the four clear areas in the "Human" VH region. The circular map of the expression vector pSVgpt at bottom shows the HindIII/BamHI insertion site for the reshaped MN-14 antibody gene just downstream from an Igh enhancer element. The map also indicates some important functional domains in the vector, including the replication origins for propagation in E. coli (colEl ori) and in mammalian cells (SV40 promoter region), and genes encoding selective markers for culturing bacterial (Ap$^r$) and mammalian (gpt) cells transformed with the vector. Expression of the antibody gene in this case is mediated by the Ig promoter indicated by the solid circles near the HindIII site in the maps of the antibody genes.

Notwithstanding past failures to develop an effective non-HAMA-inducing anti-CEA antibody having the CEA-binding characteristics of MN-14, it has been discovered that the CDRs of the MN-14 mAb can be grafted onto the FRs of a human antibody to provide antibodies and antibody-derived reagents that have the antigen binding properties of the MN-14 anti-CEA mAb, while also exhibiting reduced induction of HAMA and augmented effector activities.

The murine anti-CEA IgG1 monoclonal antibody MN-14, and its production, have been described previously. Hansen et al., Cancer, 71:3478 (1993); Primus et al., U.S. Pat. No. 4,818,709. MN-14 meets all of the criteria of a Class III, anti-CEA monoclonal antibody, being unreactive with meconium antigen by EIA and not reacting with normal tissues.

Blocking studies are carried out according to Hansen et al. 1993, above, Losman et al., Int. Cancer, 56: 580 (1994); Hansen et al., Clin. Chem., 35: 146 (1989). Using the same conditions as described in those references for quantification of CEA, binding of humanized MN-14 may be assessed relative to a labeled MN-14 probe. A typical probe is MN-14 conjugated to horse radish peroxidase (HRP). Both labeled and unlabeled MN-14 are added to a CEA sample fixed to a solid support such as microtitre plate wells. The degree of "blocking" of labeled MN-14 binding to CEA is a direct reflection of unlabeled MN-14 activity. Using standard MN-14, the relative activity of an unknown sample of humanized MN-14 or derivatives thereof can be determined. Typically, the reactions are performed in the wells of a microtitre plate where wells are charged directly with CEA at a level of, for example, 25 µg/well or indirectly where the wells are precharged with an antibody reactive with CEA but to an epitope different than that to which MN-14 interacts; such an antibody may be the MN-15 mAb. CEA can thus be indirectly fixed to the well. A competitive binding EIA assay can then be performed with such a charged plate.

Alternate to the aforementioned HRP-labeled mAbs, antibodies can be radioiodinated conventionally with, for example, $^{131}$I by the chloramine-T method to a specific activity of about 10 mCi/µg, and free radioisotopes removed by chromatography on acrylamide gel columns (see Hansen et al., 1993, above).

Molecular biological techniques suitable to carrying out the invention as herein described also are known to those skilled in the art. Suitable teachings are described in numerous manuals and primary publications, including inter alia, Sambrook et al., MOLECULAR CLONING: A LABORATORY MANUAL, 2nd Ed., Cold Spring Harbor Laboratory Press, Cold Spring Harbor, N.Y. (1989), PROTOCOLS IN MOLECULAR BIOLOGY, Ausubel et al., Eds., Green Publishing Associates and Wiley-Interscience, John Wiley and Sons, New York (1987, 1988, 1989), which are herein incorporated by reference in their entirety including supplements.

MN-14 light and heavy chain CDRs disclosed herein, and modified MN-14 CDRs can be integrated into other antibodies using well-known recombinant techniques, such as those described in the above references.

Specific methods suitable to this end are shown below in the examples. Based on the amino acid sequences set forth herein, oligonucleotides encoding MN-14 CDRs can be synthesized. Oligonucleotides that encode modified CDRs may be made, as well as those that encode exactly the amino acid sequences herein set forth. Also, the oligonucleotides may contain nucleotides in addition to those of an MN-14 CDRs, to facilitate cloning, for instance. Oligonucleotide synthesis techniques are well known, and can be carried out on automated equipment available from a number of manufacturers. Moreover, oligonucleotides of any specified sequence can be obtained commercially.

Oligonucleotides encoding the MN-14 CDRs and/or specific FR residues. or representing the complementary strand thereof, may be used to introduce codons for these residues into VH or VK DNA by site-directed mutagenesis provided that the ends of the oligonucleotides, generally 12 nucleotides, are designed to anneal perfectly to the template DNA. The template DNAs are typically single-stranded DNAs representing M13 vectors that carry a variable region DNA encoding the required FRs. In one method, the mutagenic oligonucleotides are phosphorylated at their 5' ends and, together with an oligonucleotide priming 5' to variable region DNA, are annealed to the ssDNA template. The oligonucleotides are extended using T7 polymerase and the fragments linked together by T4 DNA ligase to give a complete mutant strand covering the whole variable region. Using the mutant strand as a template, multiple copies of its complementary strand can be synthesized from a suitable primer using Taq DNA polymerase in a thermal cycling reaction. Once the mutant strand has been preferentially amplified in this manner, the DNA can be amplified by conventional PCR for cloning, sequencing and expression.

Suitable antibody-encoding DNAs are illustrated by the disclosure herein, but include practically any such DNA. A variety of human antibody genes are available in the form of publically accessible deposits. Many sequences of antibodies and antibody-encoding genes have been published and suitable antibody genes can be synthesized from these sequences much as described above.

The scope of this invention encompasses all alleles, variants and mutations of the DNA sequences described herein.

CDR grafting in accordance with the present disclosure may be carried out using established techniques. Antibody-producing cell lines may be selected and cultured using techniques well known to the skilled artisan. Such techniques are described in a variety of laboratory manuals and primary publications. For instance, techniques suitable for use in the invention as described below are described in CURRENT PROTOCOLS IN IMMUNOLOGY, Coligan et al., Eds., Green Publishing Associates and Wiley-Interscience, John Wiley and Sons, New York (1991) which is herein incorporated by reference in its entirety, including supplements.

RNA may be isolated from the original hybridoma cells by standard techniques, such as guanidinium isothiocyanate extraction and precipitation followed by centrifugation or chromatography. Where desirable, mRNA may be isolated from total RNA by standard techniques such as chromatography on oligodT cellulose. Techniques suitable to these purposes are well known in the art as described in the foregoing references.

cDNAs that encode the light and the heavy chains of the antibody may be made, either simultaneously or separately, using reverse transcriptase and DNA polymerase in accordance with well known methods. It may be initiated by consensus constant region primers or by more specific primers based on the published heavy and light chain DNA and amino acid sequences.

PCR also may be used to isolate DNA clones encoding the antibody light and heavy chains. In this case the libraries may be screened by consensus primers or larger homologous probes, such as mouse constant region probes. The necessary techniques are well known to those of skill in the art, are set forth in the foregoing Sambrook and Ausubel references and are illustrated by the examples set forth below.

cDNAs that encode the light and the heavy chain of an antibody can be propagated in any suitable vector in any suitable host prior to isolation of the CDR. Often the clones will most conveniently be propagated for this purpose in *E. coli* as illustrated in the examples below. However, a variety of other vectors and host cells well knowN to those of skill profitably may be employed in this aspect of the invention. A variety of such vectors are described in the foregoing references.

DNA, typically plasmid DNA, may be isolated from the cells, restriction mapped and sequenced in accordance with standard, well known techniques set forth in detail in the foregoing references relating to recombinant DNA techniques.

DNAs encoding antibody heavy and light chains and fragments thereof in accordance with the vector are used to construct chimeric and CDR-grafted humanized MN-14 antibodies.

Figure 1A:
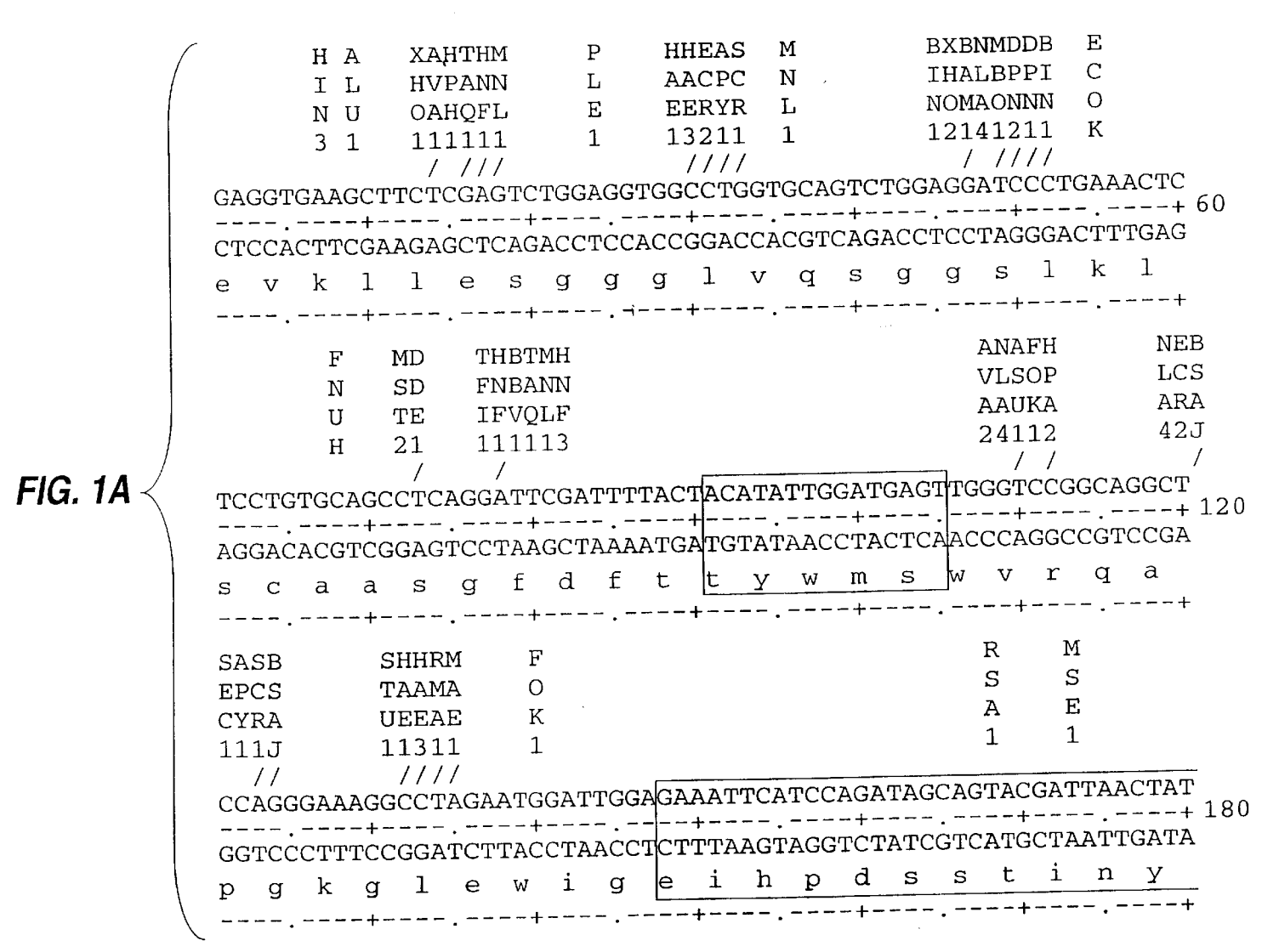

The CDRs of the MN-14 anti-CEA mAb are herein identified and described, and illustrated in FIGS. 1A & 1B and 2A & 2B (SEQ. ID NOS. 2 and 4, respectively) Using these sequences, CDRs of the MN-14 heavy and light chain can be synthesized for use in the present invention. It is not necessary to reclone MN-14 CDRs from a natural source. The DNA and amino acid sequences are set forth herein. Oligonucleotide synthesis techniques suitable to this aspect of the invention are well known to the skilled artisan and may be carried out using any of several commercially available automated synthesizers. In addition, DNAs encoding the CDRs set forth herein can be obtained through the services of commercial DNA synthesis vendors.

Polynucleotides synthesized in accordance with this aspect of the invention may include those not derived from an MN-14 CDR as well as those that make up the CDR. The additional bases may be included to facilitate joining the CDR to the FRs from a heterologous source. They may comprise restriction sites or overlapping complementary regions for this purpose. The synthesis of longer, double-stranded DNAs from shorter, overlapping, single-stranded DNAs is well known to those of skill in the art. Likewise, well known is the end-to-end joining of DNAS, including blunt-ended DNAs and those with at least partially overlapping complementary termini. These techniques are illustrated in the foregoing references on recombinant DNA techniques, for instance.

The CDRs of the MN-14 heavy and light chains may also be modified particularly after incorporation into a chimeric or humanized antibody using well-known recombinant DNA techniques for deleting, inserting and altering bases in a cloned or synthetic DNA or RNA. Site-specific mutagenesis techniques suitable to this end are well known to those of skill in the art, and are illustrated in the foregoing references on recombinant DNA techniques. Also illustrated are deletional and insertional techniques. These methods can be used to introduce practically any desired alteration into polynucleotides that encode the MN-14 CDRs or into other regions of a closed heavy or light chain gene.

MN-14 CDRs and modified MN-14 CDRs can be introduced into practically any set of FRs in accordance with the present invention. It will be appreciated by those of skill in the art that a variety of well known techniques for cloning and manipulating polynucleotides may be effectively employed in this regard. Such techniques are illustrated by the methods set forth in the foregoing recombinant DNA-related references.

In a particularly preferred embodiment of the present invention, MN-14 CDRs are grafted into a human antibody. It will be understood that human antibody in this context refers to any antibody that occurs in a human or an engineered antibody that has been designed, in some respect, to be compatible with the human immune system. Particularly preferred for this purpose are antibodies that, broadly, do not engender an adverse immune response in a patient. More particularly, the expression "human antibody" is intended to mean an antibody encoded by a gene actually occurring in a human, or an allele, variant or mutant thereof.

Once DNA encoding an MN-14-derived CDR-grafted antibody has been assembled from MN-14 VH and VK region DNAs and the variable regions thus formed combined with their respective light and heavy chains of human constant domains, it may be inserted into a vector for propagation and expression by conventional techniques. In this manner desired amounts of the antibody may be obtained.

The MN-14 CDR-grafted human antibody can be used in imaging applications by administrating to a subject the humanized antibody or Fab' thereof conjugated with an imaging compound or isotope.

The antibody is conjugated to a label for imaging using conventional methods. Such conventional methods include, but are not restricted to: 1) direct radioiodination of the antibody protein or fragments thereof or 2) direct attachment to the antibody or fragments thereof of metallic nuclides (see, e.g., Hansen et al., Cancer, 73: 761 (1994)). The use of bifunctional chelates that can be used to bind various diagnostic or therepeutic metals to the antibody or fragment thereof is also within the scope of the present invention (see, *Antibodies in Radiodiagnosis and Therapy,* ed. M. R. Zalutsky, 1989, CRC Press, Boca Raton, Fla., and *Cancer Therapy with Radiolabeled Antibodies,* ed. D. M. Goldenberg, 1994, CRC Press, Boca Raton, Fla.). Following the conjugation procedure and characterization of the product, satisfactorily labelled conjugates are purified to homogeneity under conditions that conform to Good Manufacturing Procedures ("GMP") appropriate to the production of diagnostic compositions for use in human patients.

The reaction of serum antibody with the MN-14 CDR-grafted antibody and imaging agent portions of the conjugate can be determined over the course of the diagnostic procedures, including the reaction of control sera obtained prior to administration of conjugate. Similar determinations are made in other patients treated with similar conjugates of MN-14 itself. The sera antibody reactive with CDR-grafted MN-14 human antibodies detected by these tests is much less than the antibody reactive with antibody portion of the conjugate in patients treated with the murine MN-14-containing conjugates.

Humanized MN-14 antibodies conjugated to aminodextran and to boron may be used for diagnostic purposes. MN-14 and CDR-grafted MN-14 antibodies can be prepared as set forth above for conjugation to an aminodextran-boron adduct. Amino-dextran-boron adducts can be prepared by reaction of a suitable boron cage compound (e.g., a 12-boron carborane suitably derivatized with an amino-dectran functional group). In a preferred embodiment, the amino-dextran is reacted with an excess of a haloacetyl acid ester or anhydride (such as iodoacetic anhydride), thereby producing an amino-dextran with a desired number of haloacetyl groups, usually ranging from 10–1000 groups, depending on the reaction conditions and the size of the amino-dextran. A suitable boron derivative such as mercaptocarborane-B12 is reacted, in a desired molar excess, with the haloacetyl-amino-dextran via an alkylation reaction. In a preferred embodiment, a number of haloacetyl groups on the boronated haloacetyl amino-dextran remain unreacted, and can be used as a "handle" to attach the adduct to protein thiol groups.

MN-14 CDR-grafted humanized antibodies and their derivatives, because of their reduced immunogenicity, are useful in therapy, for passive immunization without negative immune reactions such as serum sickness or anaphylactic shock, for localization and in vivo imaging of tumors as described above, for specific treatment of disease cells, e.g., site directed delivery of cytotoxins, immunomodulators or other pharmaceutically active molecules where local concentration of the active agent is an important factor, or the like, thereby establishing the practical utility of these humanized antibodies. As described above, for in vivo imaging, the humanized, CDR-grafted MN-14 monoclonal antibody is radiolabeled or conjugated with a metal chelator complexed with a radionuclide, e.g., iodine, ytrium, technetium, or the like, and radio-scanning techniques may be used to detect primary and metastatic CEA tumors. To that end, the radioactive antibody is injected, e.g., intravenously, and the patient scanned with a gamma imager at regular intervals. Tumors expressing CEA will take up more radioantibodies than other tissues and will be easily recognized by the imaging camera. Preferentially, monoclonal antibodies labelled with $^{131}$I are used in amounts of 3 to 10 μg representing 15 to 30 μCi per kg body weight. For therapy with cytotoxic agents, the antibodies are conjugated to any of a variety of known therapeutic agents such as doxorubicin, methotrexate, taxol, ricin A, radioactive atoms, cytoxic agents, and the like, formulating such conjugate in a pharmaceutically acceptable sterile vehicle, and administering the formulation by conventional means. The therapeutic dosages can be readily determined conventionally by the user of average skills in these arts. The therapeutic dose for mammals is between about 1 mg and 5 mg per kg body weight for the monoclonal antibodies themselves, and between 0.1 mg and 5 mg per kg body weight for conjugates with cytotoxic drugs, depending on the status of the patient and the mode of administration. Alternately, the humanized antibodies can be used in combination with components of the host's immune system, e.g., complement or cell mediated responses, in order to remove from the subject CEA-presenting cancer cells. The immune responses of patients may be monitored in accordance with the foregoing procedures. For additional procedures for radioimaging and therapy, see EP 0 323,806, Hansen et al., Cancer 71: 3478–85 (1993), and U.S. Pat. No. 4,818,709 and references contained therein, all of which are incorporated by reference.

Preferred are pharmaceutical preparations for parenteral administration, such as are described in Remington's Pharmaceutical Sciences, Mack Publishing Co., Easton, Pa., 1989. The final preparations contain from 0.0% to 50% of active ingredients. Methods for the production of such conjugates and their use in diagnostics and therapeutics are provided in, for example, Shih et al., U.S. Pat. No. 5,057,313; Shih et al., *Int. J. Cancer* 41:832 (1988); copending, commonly owned U.S. Ser. No. 08/162,912 now U.S. Pat. No. 5,443,953; and, McKearn et al., U.S. Pat. No. 5,156,840, the contents of which are incorporated by reference.

As noted above, for purposes of therapy, a humanized antibody conjugate and a pharmaceutically acceptable carrier are administered to a patient in a therapeutically effective amount. A combination of a conjugate and a pharmaceutically acceptable carrier is said to be administered in a "therapeutically effective amount" if the amount administered is physiologically significant. An agent is "physiologically significant" if its presence results in a detectable change in the physiology of a recipient patient. A targeted therapeutic agent is "therapeutically effective" if it delivers a higher proportion of the administered dose to the intended target than accretes at the target upon systemic administration of the equivalent untargeted agent.

To be therapeutically effective the conjugate and carrier may need to be administered in combination with other therapeutic agents or as part of a broader treatment regimen. Physicians are currently of the opinion that the effectiveness of targeted therapeutics can often be greatly increased when used in a combination therapy approach. For example, high-dose radioimmunotherapy for B-cell lymphomas, which causes severe hematologic toxicity when used alone, has been shown to be highly effective when used in combination with autologous bone marrow reinfusion. Press et al., "Treatment of Relapsed B Cell Lymphomas with High Dose Radioimmunotherapy and Bone Marrow Transplantation" in CANCER THERAPY WITH RADIOLABELED ANTIBODIES, Goldenberg, ed. (CRC Press, Boca Raton, 1994) ch. 17. In another example a five-fold enhancement of tumor uptake of a radiolabeled antibody is observed when the tumor is preirradiated. Leichner et al., Int. J. Radiat. Oncol. Biol. Phys. 14:1033 (1987). Mechanisms which have been shown to have the potential for improving the clinical efficacy of radioimmunotherapy are also discussed in DeNardo et al., "Overview of Obstacles and Opportunities for Radioimmunotherapy of Cancer" in CANCER THERAPY WITH RADIOLABELED ANTIBODIES, Goldenberg, Ed. (CRC Press, Boca Raton, 1994) ch. 11. Methods of developing such combination protocols, as well as to investigate dose-limiting side effects and to potentiate and amplify targeting, uptake, and beneficial side effects, are well known to skilled clinical artisans in this field and would not require undue experimentation to develop.

In vivo experiments using conjugates of the humanized MN-14 with diagnostic and therapeutic agents have been carried out with animal models and with human patients (see Example 11 below). The CDR-grafted humanized antibody conjugate exhibited a better therapeutic profile and could be used in longer treatment regimens than the parental MN-14 antibody conjugate. The CDR-grafted antibody conjugate provided a better therapeutic effect and fewer deleterious side effects than the control murine antibody conjugates.

For example, the antibody was covalently complexed to aminodextran-conjugated methotrexate using the method described by Shih et al., above using carbohydrate hydroxyl groups for derivatization purposes. In order to determine the contribution of antibody carbohydrate groups on immunoactivity, a mutation can be introduced at position 18–20 in the VK FR1 region of hMN-14 (the prefix "h" is intended to mean "humanized") so as to introduce a glycosylation site, NVT, prior to expression of the blocking gene in mammalian cells. Comparison of hMN-14 antibody with mutated hMN-14-NVT in a blocking cell binding assay (FIG. 8) has demonstrated that the carbohydrate moiety at position 18 is without influence on immunoreactivity of this humanized antibody.

Aminodextran, average molecular mass 40 kDa, is oxidized by $NaIO_4$ to form aldehydes (by the oxidation of hydroxyl groups). About 50 to 150 moles of aldehydic groups are introduced per mole of aminodextran by careful control of the reaction conditions and timing. The aldehydes then are reacted with an excess of 1,3-diamino-2-hydroxypropane to form Schiff bases with virtually all of the aldehydes. The Schiff bases are then reduced by treatment with excess $NaBH_4$. The amine-derivatized dextran then is purified by gel-exclusion chromatography.

The cytotoxic drug methotrexate (MTX) is activated by treatment with dicyclocarbodiamide, followed by reaction with N-hydroxysuccinimide, both in dimethylformamide. Activated MTX is mixed in a 50:1 ratio with the amino derivatized dextran in aqueous solution. The product provides, after purification, MTX-derivatized dextran having about 35 MTX moles per mole. The MTX adduct thus obtained is conjugated to a MN-14 CDR-grafted antibody using methods described in Shih, et al., supra. For example, the antibody carbohydrates are oxidized and the resultant aldehydes are reacted with the remaining amines on the dextran in the adduct. The Schiff-base product obtained thereby is reduced by treatment with sodium cyanoborohydride in 10-fold molar excess over antibody. The reduced antibody-dextran-MTX product is thoroughly purified prior to assay, and formulated for administration to patients.

Parental MN-14 antibody is conjugated to dextran-MTX in the same way, as a control.

The purified CDR-grafted antibody conjugate can be administered to patients with a CEA-producing cancer (see above). The response to therapy is monitored, including adverse side effects, particularly those which are mediated by the patient's immune systems. Patients treated with the CDR-grafted antibody conjugate show improved therapeutic results, decreased immune response to the agent and notably decreased immune-mediated adverse effects of therapy. Therapy with the CDR-grafted antibody conjugate can be carried out at higher dosages and for longer periods of time then with the parental murine MN-14 antibody, allowing more aggressive therapies and improved responses.

The present invention is further described by reference to the following, illustrative examples. It will be appreciated that the techniques related to isolating DNA clones encoding MN-14 light and heavy chain genes are illustrated by cloning techniques useful to isolate light and heavy chain genes of any antibody from producing cells. There is no necessity, given the disclosed sequence, to reisolate MN-14 heavy and light chain genes to carry out the invention.

It should be understood that the detailed description and the specific examples, while indicating preferred embodiments of the invention, are given by way of illustration only, since various changes and modifications within the spirit and scope of the invention will become apparent to those skilled in the art from the following illustrative description.

EXAMPLE 1

Culturing Antibody Producer Cells

A mouse/mouse hybridoma cell line producing Class III, anti-CEA monoclonal antibodies was established according to Hansen et al. (1993) above and Primus et al. (1983) above.

Cells were selected for secretion of kappa IgG1 by testing conditioned medium using standard isotyping techniques. A variety of kits for this purpose are commercially available. Such cells were screened for production of antibody by testing conditioned medium using a standard blocking assay described above. Stocks of producer cells that proved out in the assay were expanded and frozen in liquid nitrogen.

EXAMPLE 2

Isolating RNA from Producing Cell Lines

MN-14-producing cells were expanded in culture, collected by centrifugation and washed. Total RNA was isolated from the cells in the pellet according to Favaloro et al., Methods in Enzymology 65: 718 (1980) and Orlandi et al., Proc. Nat'l Acad. Sci., USA 86: 3833 (1989), which are incorporated by reference.

EXAMPLE 3 cDNA Synthesis and Amplification of the Heavy Chain Variable Region mRNA from MN-14 producing cells was used to synthesize cDNA using standard techniques of cDNA synthesis and DNA amplification by PCR, as described below. In general, the primers used for PCR included a restriction endonuclease cleavage site at their 5' ends to facilitate cloning of the amplification product. An oligonucleotide complementary to the end of the sense strand of the DNA encoding the first constant region domain of the murine IgG$_1$ heavy chain ("CH1") was used to prime first strand cDNA synthesis by reverse transcriptase. The sequence of this primer, CG1FOR, is shown in Table 1. Table 1 below provides other oligonucleotide sequences used herein.

there were also sites internal to the VH. Agarose gel analysis of the restriction fragments indicated the presence of an internal PstI site close to one end of the DNA. The PCR product was digested with HindIII and PstI, cloned into M13mp18 and 19 and the DNA sequence of the inserts of representative clones determined. The majority of the clones contained inserts of the same VH DNA.

The sequencing confirmed the presence of this additional, unexpected PstI site, which was close to the 3' end of the sequence of the CG1FOR primer partially encoding the final

TABLE 1

OLIGONUCLEOTIDE SEQUENCES

| | SEQ. ID NO. | |
|---|---|---|
| CG1FOR | 41 | 5' GGAAGCTTAGACAGATGGGGGTGTCGTTTTG 3' |
| VH1FOR | 42 | 5' TGAGGAGACGGTGACCGTGGTCCCTTGGCCCCAG 3' |
| VH1BACK | 43 | 5' AGGTSMARCTGCAGSAGTCWGG 3' |
| SH1BACK | 44 | 5' TGGAATTCATGGRATGGAGCTGGRTCWTBHTCTT 3' |
| SH2BACK | 45 | 5' TGGAATTCATGRACTTCDGGYTCAACTKRRTTT 3' |
| CK2FOR | 46 | 5' GGAAGCTTGAAGATGGATACAGTTGGTGCAGC 3' |
| VK1FOR | 47 | 5' GTTAGATCTCCAGCTTGGTCCC 3' |
| VK3FOR | 48 | 5' GTTAGATCTCCAGTTTGGTGCCT 3' |
| VK1BACK | 49 | 5' GACATTCAGCTGACCCAGTCTCCA 3' |
| VK2BACK | 50 | 5' GACRTTCAGCTGACCCAGGMTGMA 3' |
| VK3BACK | 51 | 5' GACATTCAGCTGACCCA 3' |
| VK4BACK | 52 | 5' GACATTGAGCTCACCCAGTCTCCA 3' |
| VK5BACK | 53 | 5' TTGAATTCGGTGCCAGAKCWSAHATYGTKATG 3' |
| VK6BACK | 54 | 5' TTGAATTCGGTGCCAGAKCWSAHATYGTKCTC 3' |
| VK7BACK | 55 | 5' TTGAATTCGGAGCTGATGGGAACATTGTAATG 3' |
| VK8BACK | 56 | 5' CWGAGAAATTCAGCTGACCCAGTCTC 3' |

Restriction sites incorporated in primers to facilitate cloning are underlined.

The variable region of the heavy chain ("VH") cDNA then was amplified by the PCR using the same primer, CG1FOR, and a primer based on the consensus sequence of the 5' end of VH genes (VH1BACK), as described in Orlandi et al. (1989) cited above. The PCR product of this reaction was analyzed by agarose gel electrophoresis, which, upon ethidium bromide staining and fluorescence illumination, revealed one major band of about 400 bp, as expected.

For confirmatory sequences from a second cDNA preparation, signal sequence primers were used in the PCR to allow determination of the authentic amino acids of the N-terminus. SH1BACK and SH2BACK, degenerate oligonucleotides based on heavy chain signal sequence coding regions were used in separate reactions in concert with CG1FOR. A diffuse product band was obtained from CG1FOR, SH1BACK amplification.

In order to increase the VH content of the product it was excised from low melting point agarose and amplified using SH1BACK and an oligonucleotide complementary to a fourth framework region consensus sequence, VH1FOR. This product of this reaction was a discrete band when analyzed by agarose gel electrophoresis.

EXAMPLE 4

Cloning and Sequencing DNA Encoding the MN-14 Heavy Chain Variable Region Obtained by PCR The amplification product obtained using the CG1FOR, VH1BACK primer pair was digested with HindIII and PstI separately. The cleavage sites of these enzymes are included in the PCR primers. It was preferable to determine whether two amino acids of the VH. Although several full length VH clones were obtained by this method, further PCR product DNA was cloned as PstI-PstI fragments. These clones thus contained full VH sequences but none of the constant region given by CG1FOR. A total of 16 full-length clones were obtained from the VK1BACK, CG1FOR product. In these experiments about 25% of the clones that were analyzed contained inserts unrelated to the VH region.

In order to confirm the VH sequence from a second cDNA preparation and, at the same time, to obtain the authentic, rather than primer-dictated, DNA sequence corresponding to the N-terminus of the VH, the PCR product from VH1FOR and SH1BACK primers was cloned. These primers contain BstEII and EcoR1 restriction sites, rather than the PstI and HindIII sites of CG1FOR and VH1BACK described above. The PCR product of this reaction was cloned by digesting with BstEII, filling in the BstEII ends, digesting with EcoRI, and ligating the EcoRI and blunt ends to the vector, which had been digested with EcoRI and HindII. The sequences of the cloned fragments were determined. The yield of VH fragments was relatively low, perhaps reflecting a lack of specificity in the PCR caused by degeneracy of SH1BACK. However, four of the 18 clones that were sequenced contained DNA encoding the MN-14 VH region as previously sequenced. The other inserts did not derive from VH-encoding DNA.

In all, 20 full-length MN-14 VH clones were obtained. Five transition mutations were observed amongst the sequences in the MN-14 VH region clones. These mutations are likely to have been introduced during amplification as a result of misincorporation by Taq polymerase.

EXAMPLE 5

Analysis of the Amino Acid Sequence of the Heavy Chain Variable Region of MN-14

Figure 1B:
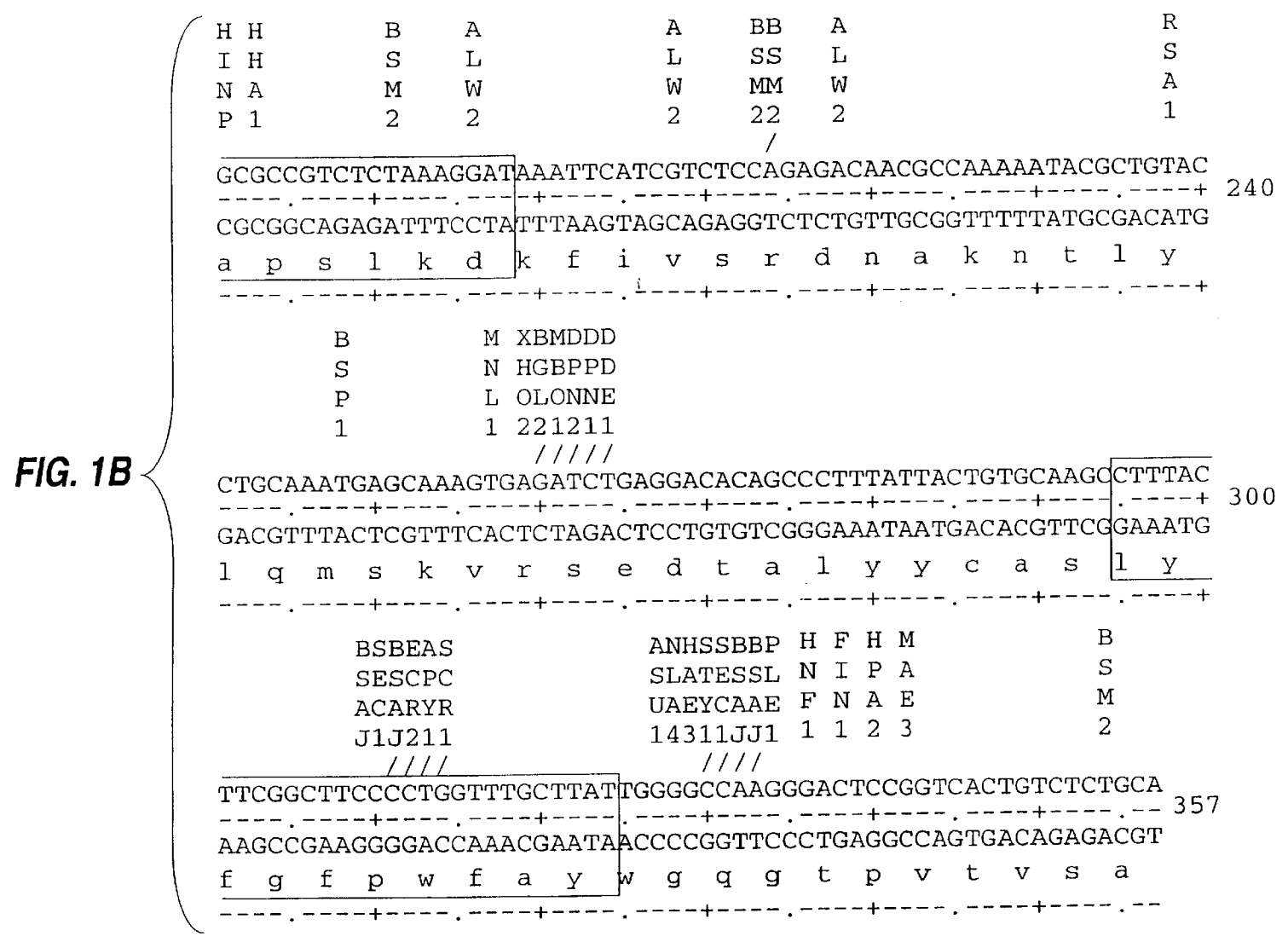

The amino acid sequence of murine MN-14 heavy chain variable region, translated from the VH DNA sequence, is shown in FIGS. 1A & 1B (SEQ. ID. NOS. 1 and 2). Comparison of this sequence with sequences representing the murine VH subgroups indicated that the variable heavy region of MN-14 belongs to subgroup IIIB (see, Kabat et al. *SEQUENCES OF PROTEINS OF IM OLOGICAL INTEREST,* U.S. Government Printing Office, 1987).

The MN-14 CDR sequences are different from any of those reported by Kabat et al. (1987), supra. Furthermore, the amino acids at four positions in the MN-14 heavy chain VH framework regions are different from those in the framework regions of other subgroup IIIB VH sequences. These four substitutions (Ser 14, Thr 30, Ser 98 and Pro 108) have been observed in other murine VH regions outside the IIIB VH subgroup, however, with the proline in Kabat position 108 being the most unusual.

Any unusual residues in the VH or VK may represent somatic mutations which proved advantageous to the binding of murine MN-14.

EXAMPLE 6 cDNA Synthesis and Amplification of DNA Encoding the MN-14 VK cDNA encoding the kappa light chain of MN-14 was cloned in much the same fashion as the cDNA encoding the variable region of the heavy chain, as described above. Several primers were used to prime reverse transcriptase for synthesis of the first strand of the kappa chain cDNA. The sequence of one primer, CK2FOR, was derived from the sequence of the 5' end of the constant region of kappa light chain genes ("CK"). The sequences of two other primers, VK1FOR and VK3FOR, were based on the sequence of the 3' end of the variable region of kappa light chain genes ("VK").

The first strand DNA product was amplified by PCR using a number of primer pairs. Synthesis in one direction was primed by the primers used to make the first strand. Polymerization in the other, "backward," direction initiated from a series of kappa light chain-specific primers which had sequences based on either the sequence at the 5' end of the VK region, VK1BACK, VK2BACK, VK3BACK, VK4BACK and VK8BACK, or the sequence encoding the last four amino acids of the signal peptide and the first four amino acids of the variable region, VK5BACK, VK6BACK and VK7BACK. In addition, cDNA primed by CK2FOR also was amplified using VK1FOR and VK8BACK.

The amplification products were analyzed by gel electrophoresis in the manner described in the Examples above. The products from the reactions primed by VK1BACK, VK3BACK, VK5BACK, VK7BACK and VK8BACK gave rise to the expected 350 bp band.

EXAMPLE 7

Cloning and Sequencing the MN-14 Kappa Light Chain Variable Region Obtained by PCR Selected PCR products were cloned into M13mp18 and 19 using the restriction sites included in the amplification primers in a manner similar to that described for VH in Example 4 above. Nucleotide sequencing revealed that most inserts were not VK-related. This is not uncommon when attempting to clone VK cDNAs and it appears to be more difficult to design VK-specific primers than VH specific primers.

From the VK1FOR/VK8BACK combination, a VK cDNA insert was obtained, but this did not yield a functional VK due to a frameshift within the cDNA encoding $CDR_{L3}$ and absence of the invariant Cys at position 23. This VK cDNA has been isolated from other hybridoma cells and it is derived from the Sp2/0 fusion partner. CK2FOR/VK1BACK product yielded a further four different aberrant VK cDNA inserts, in this case lacking the conserved residues of framework 4. A fifth VK insert obtained using this primer pair was that of a functional VK with the exception of a frameshift at the 3' end of VK1BACK, a phenomenon apparently due to mismatch-induced slippage of the primer. This problem may be avoided by the use of VK8BACK which does not extend as far into the VK gene. However, analysis of further clones from VK1FOR/VK8BACK product did not yield the desired insert.

In order to amplify preferentially the putative VK, VK3FOR was designed from its genuine fourth framework sequence, and synthesized as an alternative to VK1FOR. This strategy proved successful when amplification of VK3FOR-primed cDNA with VK3FOR and VK8BACK yielded 4 clones containing the desired VK.

The DNA and amino acid sequence of the murine MN-14 kappa light chain variable region is set out in FIGS. 2A & 2B (SEQUENCE ID. NOS. 3 and 4). This MN-14 VK can be placed in Kabat's VK subgroup V. Only 3 residues in the MN-14 VK framework regions (Met 10, Val 66 and Thr 76) do not appear in other members of this subgroup. Met 10 and Val 66 are the most unusual of the three. They are not found in any murine VK listed in Kabat. None of the MN-14 VK CDRs are previosuly-reported sequences in Kabat.

EXAMPLE 8

Figure 4:
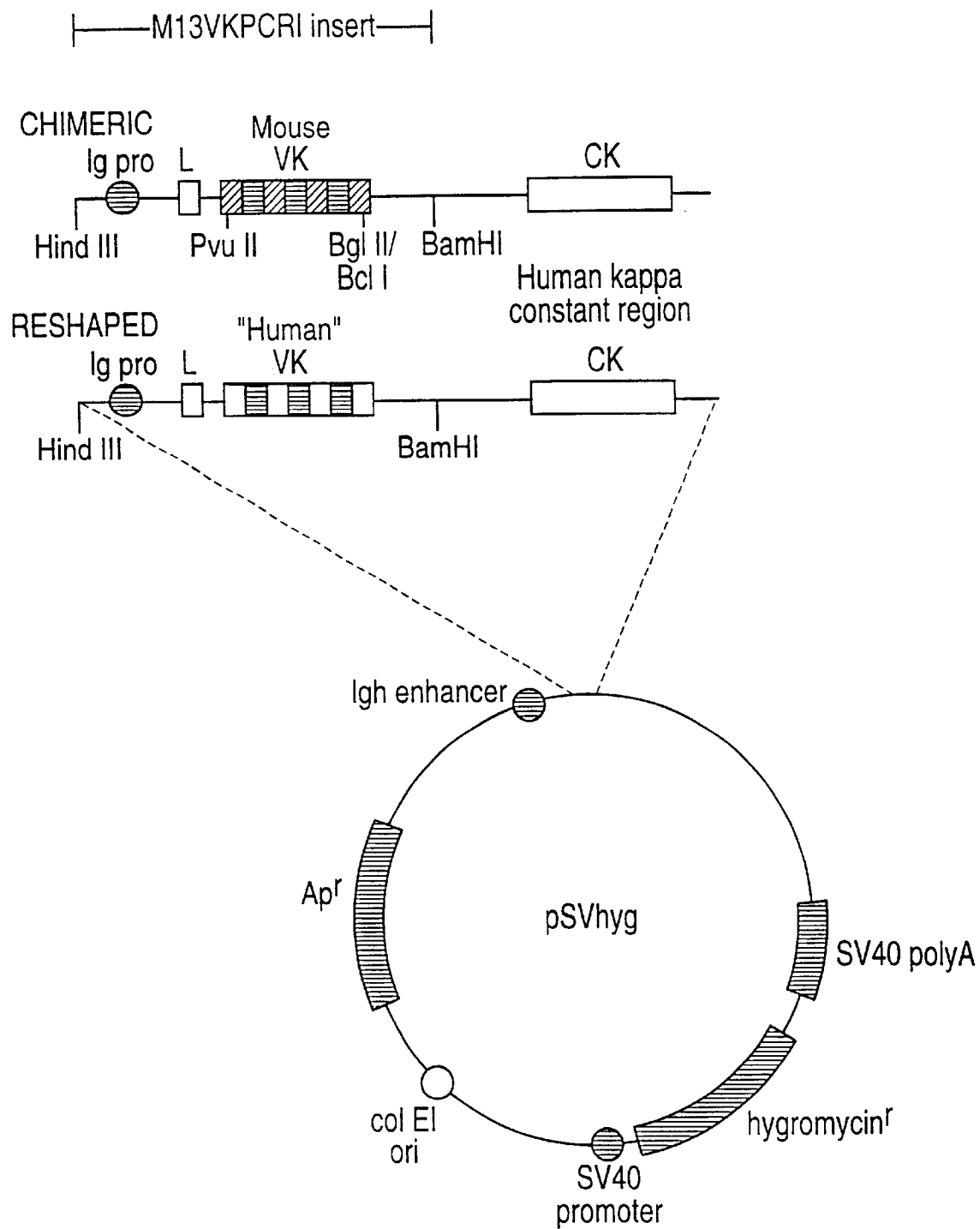
FIG. 4 shows a vector for the expression of chimeric or humanized MN-14 kappa chain gene. The diagram shows a chimeric and a reshaped MN-14 kappa light chain gene and the pSVhyg expression vector. The diagram at top, labelled "CHIMERIC," is a map showing DNA encoding the MN-14 mouse kappa light chain variable region ("VK") joined to DNA encoding a human kappa constant ("CK") region. In the mouse VK region the three CDRs are indicated by the three dark areas and the FRs are indicated by the four stippled areas. The middle diagram, labelled "RESHAPED" shows the humanization of the MN-14 VK region in which the mouse FRs have been replaced by human FRs, which are indicated by the four clear areas in the "Human" VK region. The circular map of the expression vector pSVhyg at bottom shows the HindIII/BamHI insertion site for the reshaped MN-14 antibody gene just downstream from an Igh enhancer element. The map indicates some important functional domains in the vector, including the replication origins for E. coli (col El ori) and mammalian propagation (SV40 promoter region), and genes encoding selective markers for culturing bacterial (Ap$^r$) and mammalian (gpt) cells transformed with the vector. Expression of the antibody gene in this case is mediated by the Ig promoter schematized by the solid circles near the HindIII site in the maps of the antibody genes.

Grafting of the MN-14 VH and VK CDRs into Variable Regions of Human Antibody 8.1. Construction of Chimeric Antibody Expression Vectors In the production of a chimeric antibody consisting of murine variable regions and human constant regions, testing alongside the parent mouse antibody served to check that the correct variable region cDNAs have been isolated. A successful chimeric antibody also acts as a useful control when assessing the binding of humanized versions. The scheme used in cloning the variable regions for expression is described by Orlandi et al. (1989) supra, and is illustrated in FIGS. 3 and 4.

VH DNA was amplified from the M13 clone MNVH41 using the PCR with oligonucleotides VH1BACK and VH1FOR. The PstI and BstEII restriction sites in the primers allowed the VH to be inserted into M13VHPCR1 in the correct context for expression. At this point, the internal BamHI restriction site of the VH was removed by site directed mutagenesis. The reaction product, which encompassed the entire HindIII-BamHI fragment of M13VHPCR1 was cloned into pSVgpt and the VH sequence confirmed.

The human IgG1 constant region gene, published by Takahashi et al., *Cell,* 29: 671–679 (1962) above then was added to the construct as a BamHI fragment, which yielded the vector referred to as pSVgptMN14MuVHHuIgG1.

VK DNA was similarly obtained from the M13 clone MNVK154 by PCR amplification with the primers VK8BACK and VK3FOR and the PvuII, BglII-digested product cloned into M13VKPCR1, whereupon the sequence of the variable region was checked. The HindIII-BamHI fragment was excised from RF DNA and transferred to the plasmid pSVhyg. The construct already contains a human kappa constant region gene as described in Hieter et al., *Cell,* 22: 197–207 (1980). The final vector thus obtained was designated pSVhygMN14MuVKHuCK.

8.2 Expression and Testing of the Hybrid Antibody

The HindIII-BamHI fragment of M13KLHuVHAIGA was inserted into a plasmid pSVgpt to yield the expression vector pSVgptKLHuAIGAHuIgG1. Similarly, the HindIII-BamHI fragment of M13HuVK was inserted into the plasmid pSVhyg to yield the expression vector pSVhygMN14REIHuVKHuCK. About 5 µg pSVgptMN14MuVHHuIgG1 and 10 µg pSVhygMN14MuVKHuCK DNAs were linearized with Pvul and transferred into about $10^7$ subconfluent SP2/0 myeloma cells by electroporation conventionally using a BioRad Model 165BR1160 Gene Pulser Electroporator with a single pulse of 170 V, 960 µF. Cells were selected for the expression of the gpt gene in 24-well plates by addition of mycophenolic acid and xanthine to the DMEM+10% FCS growth medium.

Wells which contained colonies of surviving cells were identified. The supernatant medium was removed from these wells and assayed for human antibody. Colonies that secreted antibodies were expanded to give 0.5 L of conditioned medium for isolation of larger amounts of antibody.

Antibody was purified conventionally from the medium by protein-A agarose affinity chromatography, initially. The purified antibody was characterized further with reference to native MN-14 antibody, human antibodies and other controls.

The antibody was also characterized by its reaction profile in a MN-14 blocking assay, which provided an informative comparison of CEA binding affinities of the hybrid antibodies with CEA binding by the MN-14 murine antibody which served as a positive control.

8.3 Humanization of the MN-14 Antibody

Figure 5A:
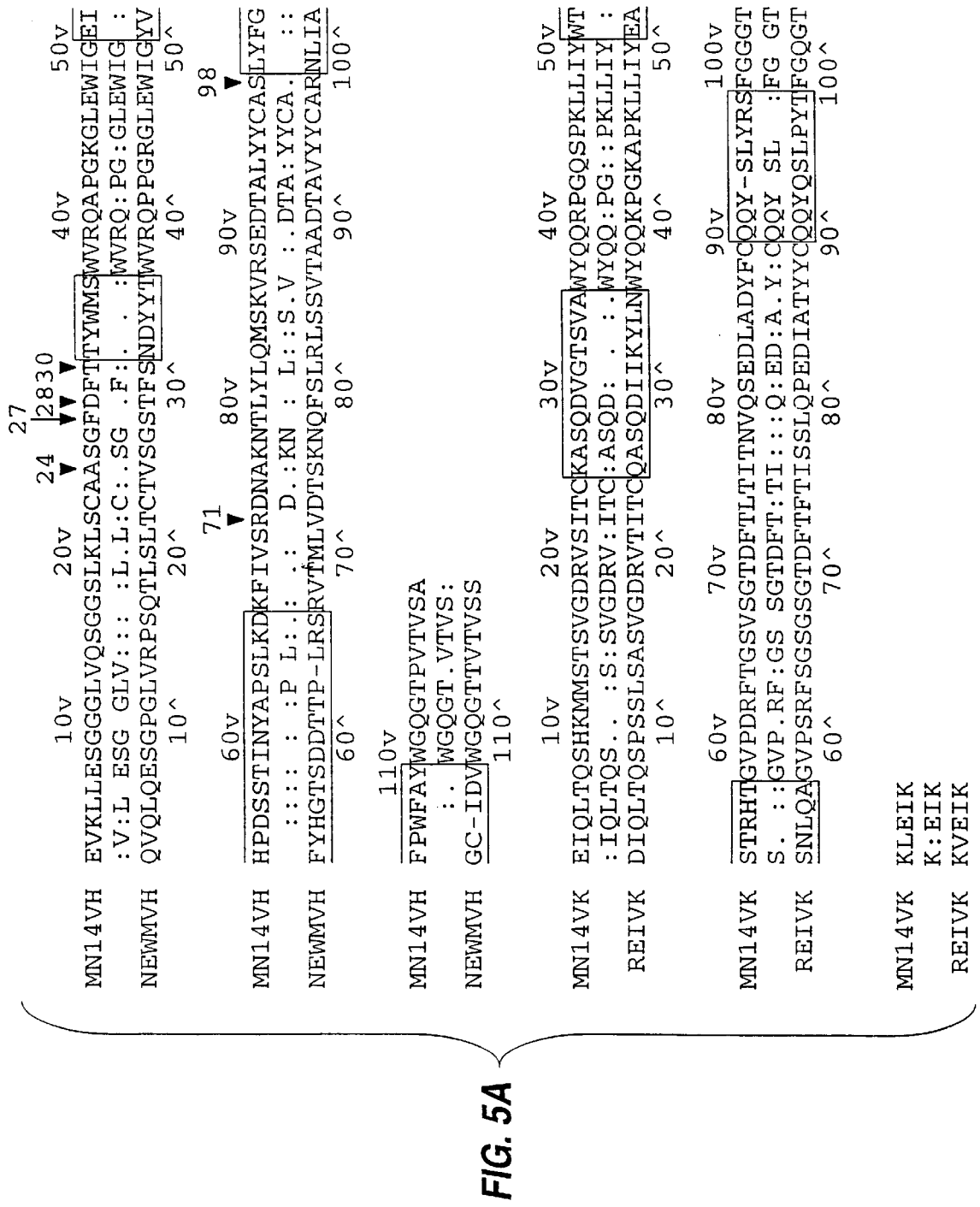
FIGS. 5A and 5B shows the alignments of the murine MN-14 variable regions (SEQ. ID. NOS. 2 and 4) with the human variable regions NEWM VH (SEQ. ID NO. 5) and REI VK (SEQ. ID NO. 6) (FIG. 5A). and with the human KOL VH region (SEQ. ID NO. 7, FIG. 5B). CDRs are boxed, and the murine VH FRs, which are incorporated into the humanized VH, are marked with their positions according to the numbering system of Kabat et al. SEQUENCES OF PROTEINS OF IMMUNOLOGICAL INTEREST, U.S. Government Printing Office, Washington, D.C., 1987. Murine residues outside the CDRs that were included in the KLHuVH are indicated by a filled circle.
Figure 5B:
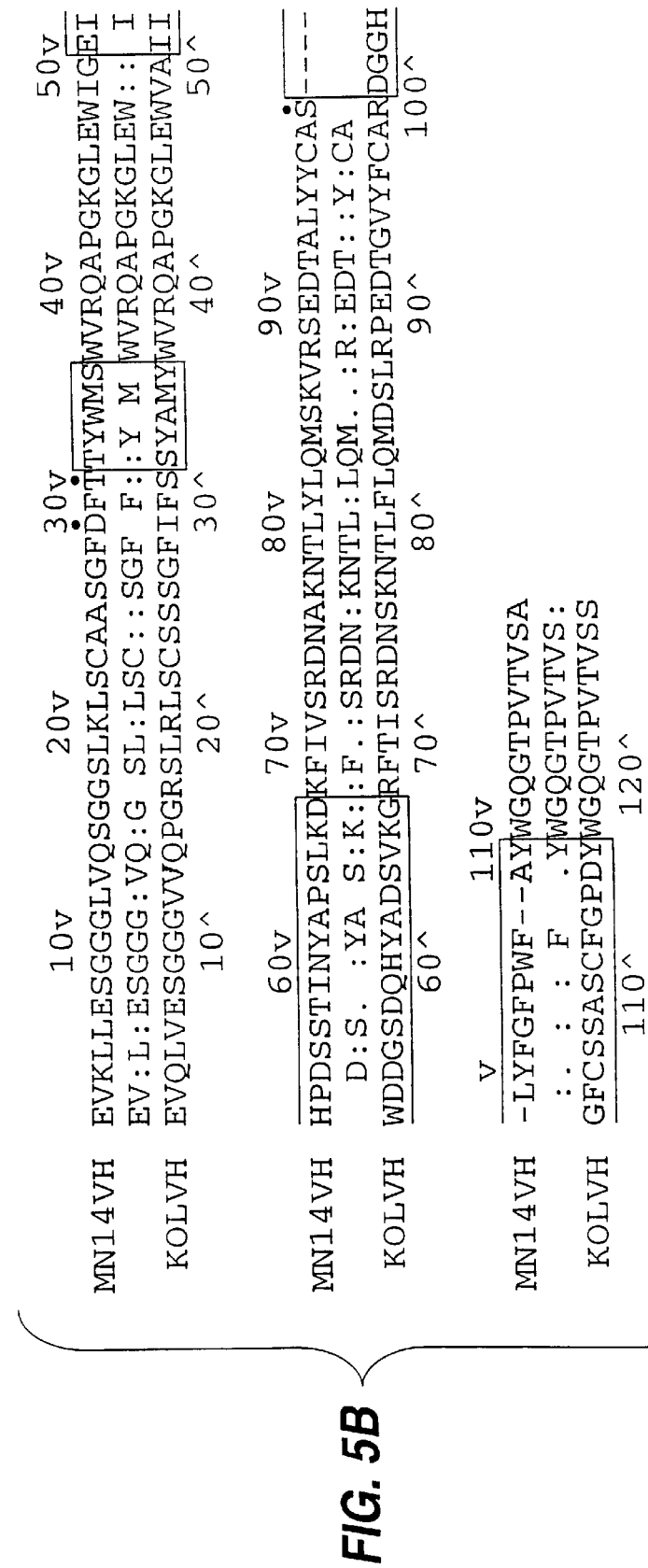

The human NEWM VH, KOL VH and REI VK frameworks were chosen as the basis for reshaping the antibody, as they are likely to be tolerated in humans. Alignments of the MN-14 VH (SEQ. ID NO. 2) and VK (SEQ. ID NO. 4) with these human variable regions are shown in FIGS. 5A & 5B (SEQ. ID. NOS. 5–7).

A. NEWM Based Humanization

The starting points for the introduction of MN-14 CDRs are DNAs encoding the required FRs and irrelevant CDRs. These template variable regions are in a form compatable with the expression vectors used, that is, within HindIII-BamHI fragments, that also include promotor regions, signal peptide and intron DNA (FIGS. 3 and 4). For the NEWM VH version, the template is M13VHPCR1 (Orlandi et al, above, and section 8.3 below). A derivative of this template, containing KOL FRs and irrelevant CDRs, was used to generate the KOL coding region. A derivative of M13VKPCR1 (Orlandi et al. above) was used in the creation of the HuVK vector. The resulting vectors were termed M13NMHuVH, M13KLHuVH and M13HuVK. The HindIII-BamHI fragments containing the humanized MN-14 variable region DNAs were transferred from these M13 vectors to the expression vectors essentially as described for the construction of the chimeric MN-14 expression vectors in Example 8.1.

The NEWM FR is described in Poljak et al. *Biochemistry* 16: 3412–20 (1977). Construction of a hMN-14 with an affinity for CEA comparable to that of its murine counterpart was achieved in a stepwise approach. Production of the chimeric antibody provided a useful control when assessing the binding of the humanized versions. The human NEWM VH and REI VK frameworks were initially chosen as the basis for reshaping the antibody as they are known to be tolerated in man. MN-14 residues Phe27, Asp28 and Thr30 were retained because, although not part of the Kabat's hypervariable region, CDR1 residues 31–35, those amino acids are part of the CDR1 structural loop (Chothia et al., *J. Mol. Biol.* 176: 901–917 (1987)). In addition, the following residues were also selected for incorporation into the humanized VH for the following reasons: Ala24, this residue contacts CDR1; Arg71, the side chain of this residue pokes through the center of the domain to interact with CDRs 1 and 2; substitution of the smaller Val may alter the conformation of these CDR loops; and, Ser94, the majority of antibodies have Arg in this position where it is thought to interact with an Asp residue on CDR3, and the inclusion of the Arg of NEWM could create an unwanted interaction with the murine CDR. Other changes were made to this version (NMHuVH) in three areas corresponding to regions which had been proved important in other reshaped molecules. These changes were:

(i) Gln77Phe78Ser79 to ThrLeuTyr (NMHuVhHTLY, SEQ. ID NO. 9)

(ii) Ser82Thr83Ala84Ala85 to LysArgSerGlu (NMHuVhHKRSE, SEQ. ID NO. 10)

(iii) Arg66Val67Thr68Met69Leu70 to LysPheIleValSer (NMHuVhKFIVS, SEQ. ID NO. 11)

The alignment of the different versions of the NEWM VH frameworks (SEQ. ID NOS. 5 and 8–11) with the MN-14 VH (SEQ. ID NO. 2) is shown in FIGS. 6A, 6B & 6C. Each of these versions has been paired with the same HuVK. The inclusion of either the TLY or KFIVS motifs gave about a two-fold improvement.

There are 2 differences from the NEWN framework sequences given in Kabat et. al (1987) above: S107 to T and L108 to T. Kabat lists residue 1 as PCA and residues 5 and 6 as E or Q.

B. KOL Based Humanization

In parallel to the use of NEWM VH, we have also reshaped the human KOL VH. KOL VH is described in Schmidt et al., *Z. physiol. Chem,* 364: 713–747 (1987). The FR used for humanizing the antibody is as given in Kabat. The original version of the KOL-based VH contained the MN-14 CDRs, as defined in terms of residue variability (Kabat et al., above) and three additional murine residues. As with the NEWM VH, two of these substitutions were made because the actual peptide CDR1 structural loop, which extends from the β-sheet framework, consists of residues 25 to 32 (Chothia et al. 1987, above). Changes at positions 28 and 30 allowed this loop to be transplanted as a whole from the murine antibody. MN-14 residue 94 was included because the Arg residue of the KOL VH is involved in a salt bridge with Asp110 and, like with the NEWM VH, it was felt that retention of Arg 94 might perturb the MN-14 CDR3 structure. The side-chain of residue 94 may also interact with residues of CDR1. Other changes made to this basis MN-14 KOLHuVH (SEQ. ID NO. 12) were as follows:

(i) Ser24 to Ala24 and Val48Ala49 to IleGly (KLHuVhAIG, SEQ. ID NO. 13).

(ii) Ser24 to Ala24, Val48Ala49 to IleGly and Ser74 to Ala (KLHuVhAIGA, SEQ. ID NO. 14).

(iii) Ser 24 to Ala24, VAl48Ala49 to IleGly, Ser74 to Ala and Phe79 to Tyr (KLHuVhAIGAY, SEQ. ID NO. 15).

Mutation Rationale

Ala24—The loop of CDR1 is anchored by the penetration of the side chain of residue 29 into the framework. Residue 24 is one of those with which it interacts (Chothia et al., *J. Mol. Biol.* 227: 799–817 (1992)).

Ile48Gly49—Although both these residues are adjacent to the CDR2 hypervariable region they are far removed from the actual structural loop. Both residues are completely buried (Padlan, *Mol. Immunolog.* 28: 489–498, 1991) and it was considered possible that these would effect binding via their packing interaction.

Ala74—This residue is part of the fourth loop found at the VH antigen-binding surface and its side chain is almost completely exposed to solvent (Padlan, 1991 above). Direct interaction of this residue with antigen could be envisaged.

Tyr79—Like residue 74, this residue is close to the antigen-binding site and could effect binding.

The alignment of the different versions of KOL VH frameworks (SEQ. ID NOS. 7 and 12–15) with NEWM based versions (SEQ. ID NOS. 5 and 8–11) and the murine MN14 (SEQ. ID NO. 2) is shown in FIGS. 6A, 6B and 6C.

Figure 7:
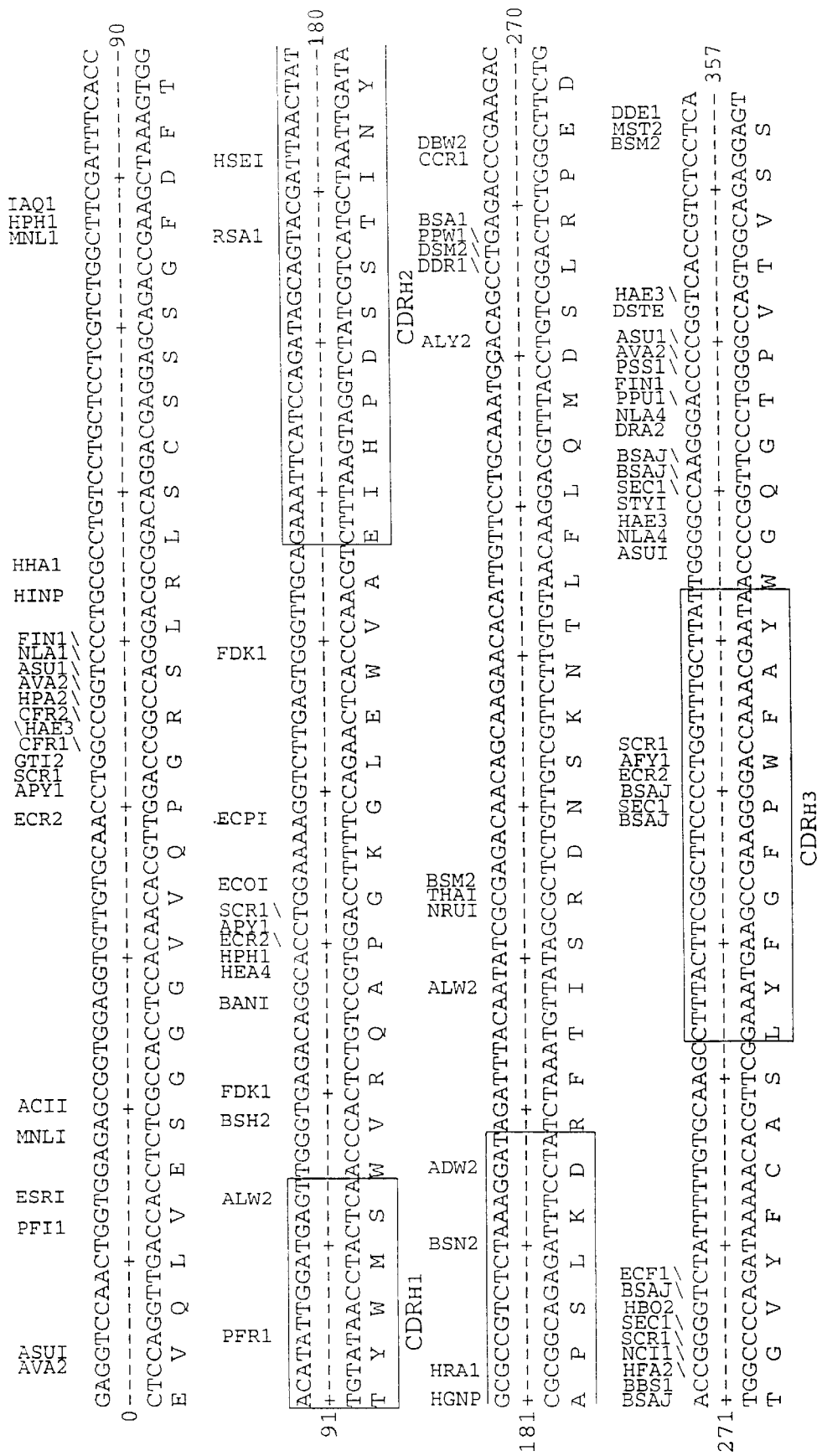
FIG. 7 shows the DNA sequence and corresponding amino acid sequence (SEQ. ID NOS. 16 and 17) of the MN-14HuVH (KLHuVh) region. CDRs are boxed.
Figure 8:
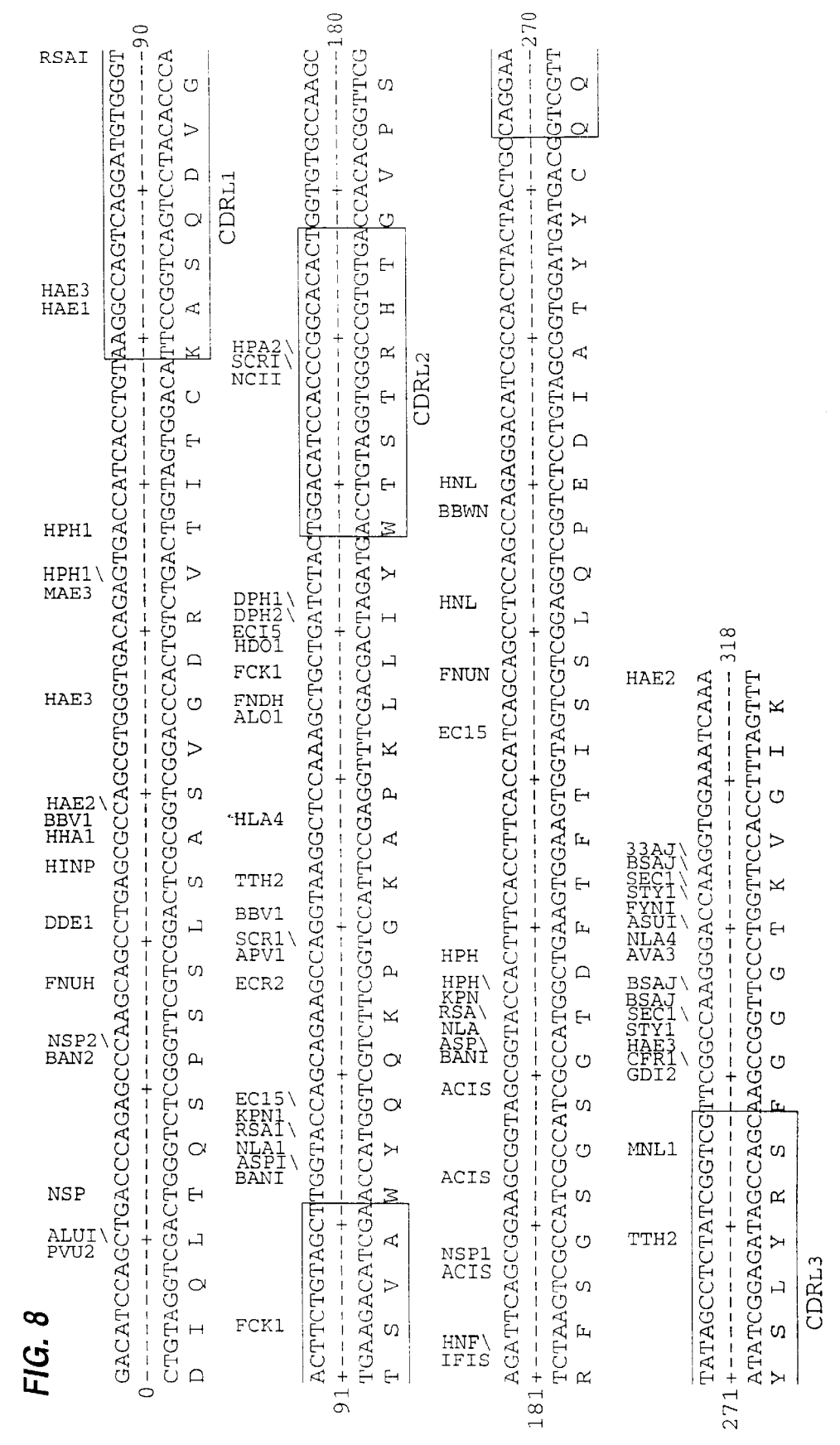

The DNA sequences and translation products of MN14HuVH and MN14HuVL are shown in FIGS. 7 and 8, respectively (SEQ. ID NOS. 16–19, respectively).

Figure 9:
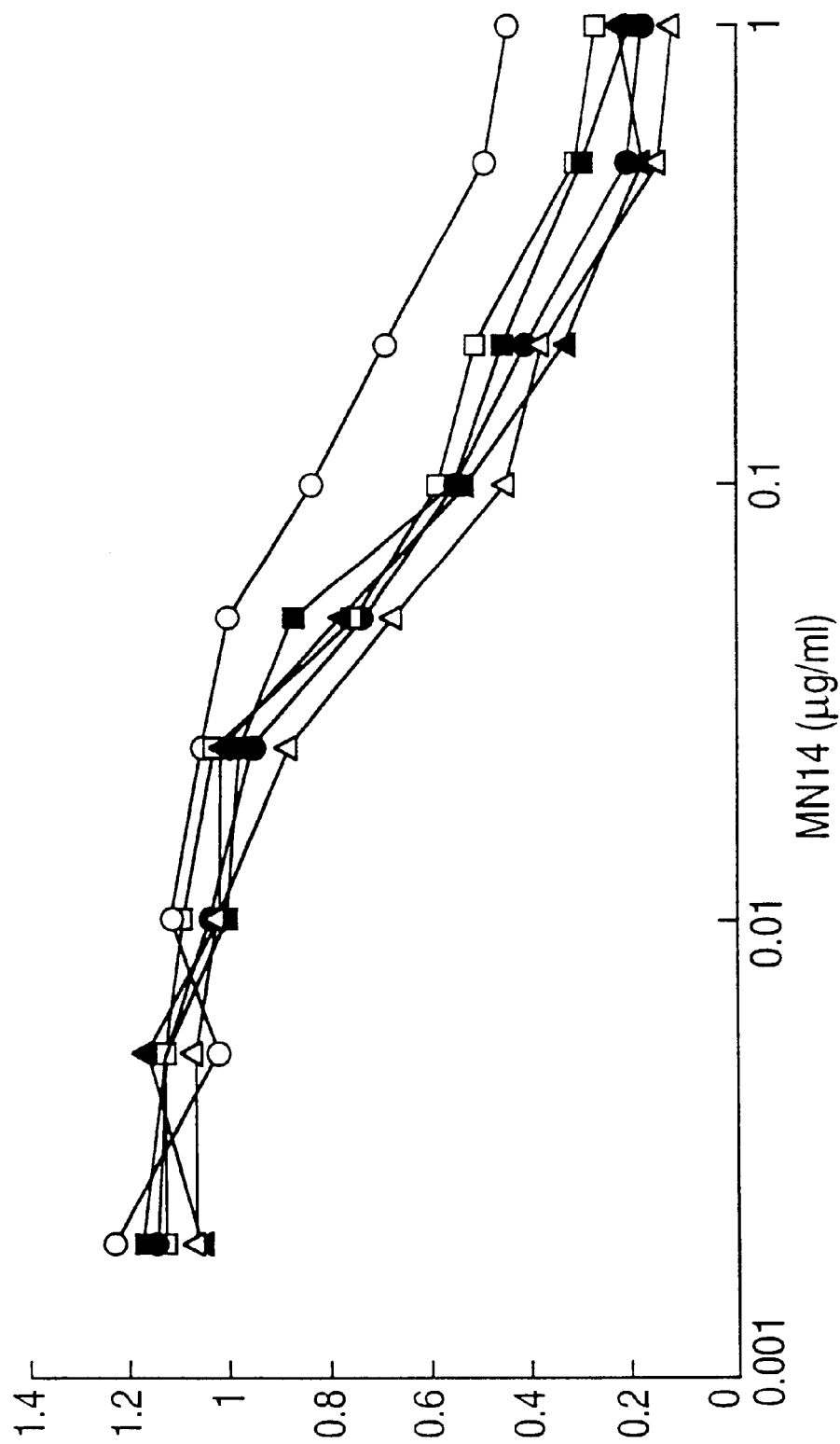
FIG. 9 is a graph of MN-14 blocking (i.e., competition) assays comparing relative binding affinities of KLHUVH variants, including: (-○-) KLHuVH/HuVK; (-■-) KLHuVHAIG/HuVK; (-●-) KLHuVKAIGAY/HuVK; (-□-) KLHuVHAIGA/HuVK; (-▲-) chimeric control; and, (-Δ-) murine control.
Figure 10:
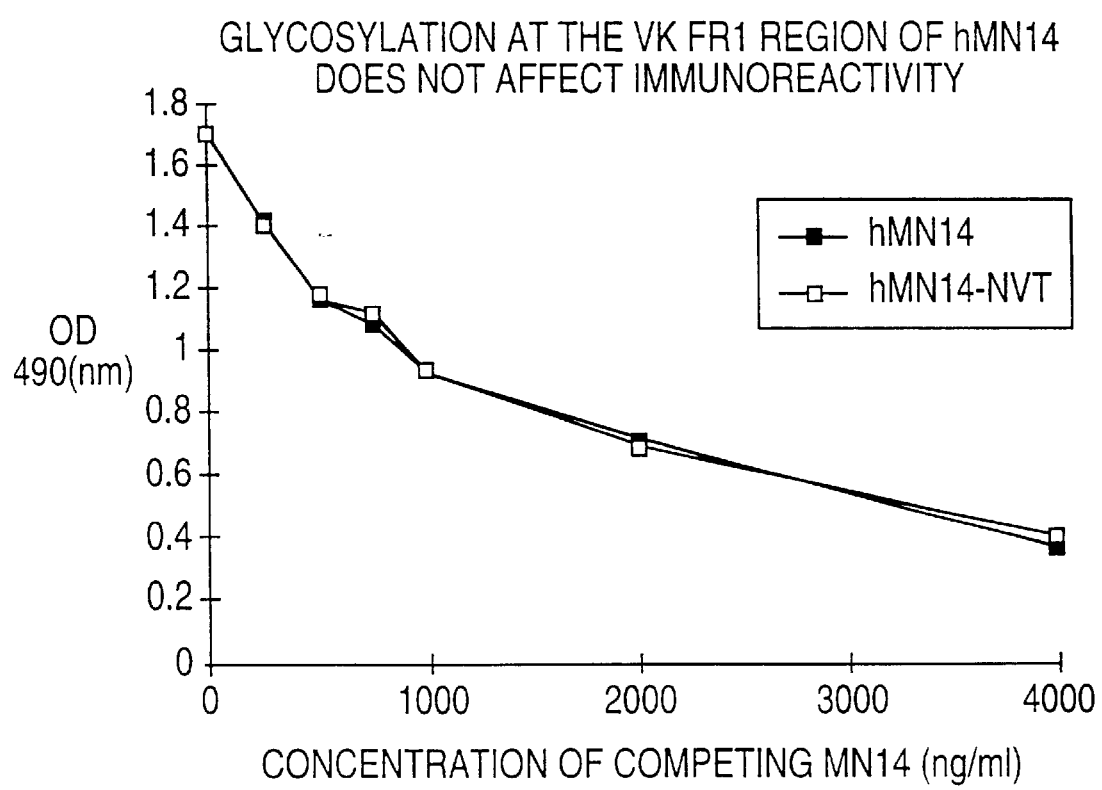
FIG. 10 shows MN-14 blocking assays comparing hMN-14 with HMN-14-NVT (glycosylated in FR 1 region).
Figure 11:
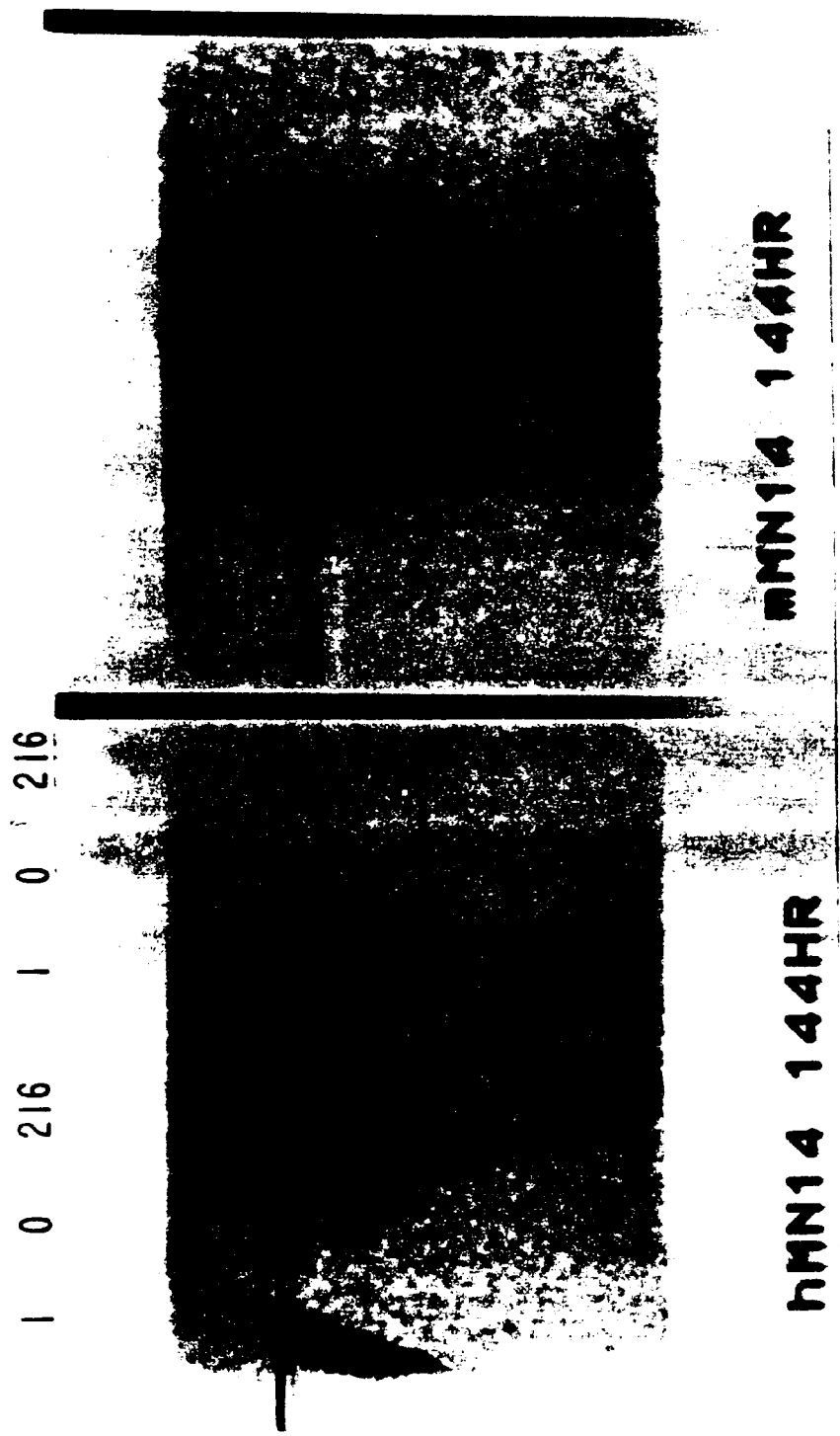
FIG. 11 is a radioautogram of the abdomen of a colon cancer patient following administration of $^{131}$I-labelled hMN14IgG (left panel) or mMN14IgG (right panel) in the same patient.

The humanized KLHUVH varients, such as antibody KLHuVHAIGA/HuVK, were purified and tested in a blocking assay carried out as follows. Antibodies were added at the indicated concentrations together with HRP-labeled MN-14 to a final volume of 0.1 ml. Following 30 mins. of incubation at 37° C., and washing to remove unbound antibodies, the relative affinities of the antibodies were determined from the remaining bound peroxidase activity. A shown by the assay data of FIG. 9, the activity of the "reshaped" (i.e., CDR-engrafted on FR) humanized antibody was similar to that of chimeric and murine positive controls.

Results obtained using supernatant fluids from cells secreting KLHuVHAIG/HuVK and KLHuVHAIGAY/HuVK antibodies suggests that these have blocking activities that are similar to that of the KLHuVHAIGA/HuVK antibody.

C. REI Based Humanization

REI VL is described in Epp et al., *Eur. J. Biochem.*, 45: 513–24 (1974). No changes were made in REI framework to improve binding. The changes from the sequences given in Kabat et al. (1987) are: M4 to L; T39 to K: Y71 to F; L104 to V; Q105 to E: and T107 to K. These changes preexisted in the template used when grafting the MN-14 CDRs and were not made specifically to improve binding. The M4 to L change incorporates a restriction site but the remaining differences eliminate unusual residues in the REI framework. A similar framework has been referred to as a consensus of huma kappa subgroup I by Foote et al., *J. Mol. Biol.* 224: 487–9 (1992)

EXAMPLE 9

Expression of MN-14 CDR-grafted Humanized Antibodies

Cells that were stably transformed for expression of the MN-14 CDR-grafted human antibodies were selected in the manner described above and cloned out to establish individual producer lines. Each of the lines was assayed to determine production of the correct antibody and to assess the efficiency of production. The antibody class was determined and the anti-CEA binding affinity assessed.

The best producers were further characterized for the overall amount of the antibody produced and, for the best of these, sequences were obtained from the mRNA to insure that the mutation has not occurred in the antibody genes during transfection, integration, propagation or selection.

EXAMPLE 10

Purification of MN-14 CDR-grafted Humanized Antibodies Expressed in Cell Culture The best producer lines of the MN-14 CDR-grafted human antibody were cultured, the growth medium collected and filtered through a 0.2 micron membrane. The antibody was then purified by protein A chromatography followed by other conventional purification steps such as ion exchange and size exclusion chromatography. The cells were pelleted and from the supernatant by conventional centrifugation. The antibody was purified from the supernatant fluid as described above.

EXAMPLE 11

Uses of Humanized MN-14 Monoclonal Antibody in Diagnoses

A. Animal Studies

The biodistribution of labeled humanized MN-14 IgG in nude mice bearing human colon cancer was determined. For radiolocalization studies, at 4–5 weeks female athymic mice (nu/nu, Harlan, Indianapolis, Ind.) were given s.c. 0.2 ml of a 10% suspension of LS174T human colon adenocarcinoma prepared from a xenograft serially propagated in an athymic mouse (Sharkey et al., *Cancer Res.*, 50: 828–34 (1990)). After waiting 2 weeks for tumor development, the mice were injected i.v. with 20 $\mu$Ci (about 2 $\mu$g) of $^{131}$-labelled humanized MN-14 monoclonal antibodies. Groups of 4–5 mice were sacrificed at intervals thereafter, and radioactivity localized in tissues according to Sharkey et al., above. The data of Table 2 show the % injected dose/g tissue and tumor:nontumor ratios.

The results show excellent tumor accretion of the antibody, with maximum accretion occurring within 2 days. Blood clearance of the hMN-14 antibody was more rapid than the parental mMN-14 antibody. In addition, there was higher uptake of hMN-14 by the spleen than there was of mMN-14, reflecting the fact that the former antibody is "foreign" to the mouse. Tumor:nontumor ratios were excellent. These results demonstrate that the inventive hMN-14 mAb is capable of targeting CEA-producing tumors.

TABLE 2

| | Percent Injected Dose Per Gram tissue (N = 4 to 5 animals) Time Post-Injection $^{131}$I-hMN-14 IgG | | | | | |
|---|---|---|---|---|---|---|
| Tissue | 4 hour | 1 day | 2 days | 5 days | 7 days | 14 days |
| LS174T | 11.8 ± 2.9 | 18.1 ± 14.9 | 32.6 ± 17.2 | 30.2 ± 13.4 | 10.6 ± 15.2 | 11.6 ± 5.6 |
| weight | 0.31 ± 0.07 | 0.37 ± 0.02 | 0.27 ± 0.08 | 0.31 ± 0.9 | 0.3 ± 0.2 | 0.40 ± 0.07 |
| Liver | 10.8 ± 2.1 | 6.0 ± 3.3 | 2.8 ± 0.5 | 0.8 ± 0.4 | 0.5 ± 0.7 | 0.08 ± 0.05 |
| Spleen | 17.0 ± 4.8 | 10.5 ± 8.8 | 4.9 ± 0.4 | 1.3 ± 0.6 | 0.6 ± 0.8 | 0.14 ± 0.09 |
| Kidney | 7.0 ± 0.8 | 3.1 ± 0.7 | 2.3 ± 0.9 | 0.9 ± 0.4 | 0.4 ± 0.6 | 0.07 ± 0.04 |

TABLE 2-continued

| | | | | | | |
|---|---|---|---|---|---|---|
| Lungs | 8.7 ± 0.4 | 3.7 ± 1.4 | 3.7 ± 1.4 | 1.4 ± 0.6 | 0.6 ± 1.0 | 0.11 ± 0.06 |
| Blood | 15.4 ± 6.6 | 5.5 ± 4.7 | 6.8 ± 4.1 | 2.3 ± 1.2 | 0.9 ± 1.8 | 0.14 ± 0.13 |

Tumor (LS174T)/Nontumor Ratios (N = 4 to 5 animals)
Time Post-injection $^{131}$I-hMN-14 IgG

| Tissue | 4 hour | 1 day | 2 days | 5 days | 7 days | 14 days |
|---|---|---|---|---|---|---|
| Liver | 1.1 ± 0.3 | 5.0 ± 5.0 | 11.1 ± 4.7 | 39.5 ± 7.5 | 24.6 ± 4.8 | 160 ± 28 |
| Spleen | 0.7 ± 0.3 | 4.2 ± 4.6 | 6.6 ± 3.4 | 24.7 ± 7.8 | 15.8 ± 4.4 | 91 ± 21 |
| Kidney | 1.7 ± 0.5 | 5.3 ± 3.5 | 13.3 ± 3.6 | 36.1 ± 4.0 | 38.4 ± 12.9 | 173 ± 41 |
| Lungs | 1.4 ± 0.4 | 4.2 ± 2.2 | 8.2 ± 2.1 | 22.3 ± 2.1 | 25.4 ± 7.3 | 112 ± 15 |
| Blood | 0.9 ± 0.5 | 3.7 ± 0.9 | 5.4 ± 1.4 | 14.2 ± 2.9 | 26.0 ± 12.9 | 111 ± 35 |

B. Clinical Studies with $^{131}$I-labeled Humanized MN-14 IgG

Patients were entered into an Institutional Review Board-approved protocol at the Center for Molecular Medicine and Immunology, Newark, N.J. for a pilot investigation of the targeting and pharmacokinetic behavior of the humanized MN-14 IgG. In the case the results of which are shown in FIG. 12, the male patient had colorectal cancer that had metastasized to the liver. He was injected i.v. with $^{131}$I-hMN-14 IgG (8 mCi, 0.6 mg antibody) and images were taken over a six day period. The patient was subsequently injected with an identical dose of mMN-14 IgG. The images shown in FIG. 12 shaw the anterior abdominal view about 140 h after each injection. The images are adjusted to exactly the same intensity so that they are directly comparable. The results indicate that the humanized antibody is taken up by the CEA-producing tumor as well as the parental murine antibody. These experiments establish the practical utility of diagnosing human CEA-producing colon cancers with the inventive humanized MN-14 mAb.

What is claimed is:

1. A method for treating a patient comprising administering a conjugate to said patient in an effective amount for treatment, wherein said conjugate comprises:

a therapeutic agent bound to a humanized Class III, anti-CEA, monoclonal antibody (mAb) or a fragment thereof, wherein the complementarity-determining regions (CDRs) of said humanized mAb are CDRs from a parental murine Class III, anti-CEA mAb, wherein the light chain variable region comprises CDRL1 comprising KASQDVGTSVA (SEQ ID NO:20), CDRL2 comprising WTSTRHT (SEQ ID NO:21), and CDRL3 comprising QQYSLYRS (SEQ ID NO:22), and the heavy chain variable region comprises CDRH1 comprising TYWMS (SEQ ID NO:23), CDRH2 comprising EIHPDSSTINYAPSLKD (SEQ ID NO:24) and CDRH3 comprising LYFGFPWFAY (SEQ ID NO:25), and each of the framework regions (FRs) of the light and heavy chain variable regions is from a human antibody, wherein said humanized mAb retains the binding specificity of said parental murine Class III, anti-CEA mAb.

2. The method of claim 1, wherein said therapeutic agent comprises a cytotoxic agent or an immunomodulator.

3. The method of claim 2, wherein said cytotoxic agent comprises doxorubicin, methotrexate, taxol, ricin A or a radionuclide.

4. The method of claim 3, wherein said radionuclide comprises $^{131}$I.

5. The method of claim 1, further comprising administering a second therapeutic agent to said patient.

6. The method of claim 5, wherein said second therapeutic agent is doxorubicin, methotrexate, taxol, ricin A, or a radionuclide.

7. The method of claim 2, wherein said cytotoxic agent is a radionuclide, and said method further comprises administering a second therapeutic agent or performing a treatment regimen to said patient.

8. The method of claim 7, wherein said treatment regimen is a bone marrow reinfusion.

9. The method of claim 7, wherein said radionuclide is $^{131}$I.

10. The method of claim 1, wherein:

(a) the light chain variable regions correspond to the formula:

FRL1-CDRL1-FRL2-CDRL2-FRL3-CDRL3-FRL4, wherein each FR is a different framework region of a human antibody, and FRL1 comprises a region of about 23 amino acids that occurs naturally in the FRL1 of a human antibody;

FRL2 comprises a region of about 15 amino acids that occurs naturally in the FRL2 of a human antibody;

FRL3 comprises a region of about 32 amino acids that occurs naturally in the FRL3 of a human antibody;

FRL4 comprises a region of about 10 amino acids that occurs naturally in the FRL4 of a human antibody; and (b) the heavy chain variable regions are characterized by the formula:

FRH1-CDRH1-FRH2-CDRH2-FRH3-CDRH3-FRH4, wherein each FR is a different framework region of a human antibody, and FRH1 comprises a region of 28–32 amino acids that occurs naturally in the FRH1 of a human antibody;

FRH2 comprises a region of 12–16 amino acids that occurs naturally in the FRH2 of a human antibody;

FRH3 comprises a region of 30–34 amino acids that occurs naturally in the FRH3 of a human antibody; and FRH4 comprises a region of 9–13 amino acids that occurs naturally in the FRH4 of a human antibody.

11. The method of claim 10, wherein

FRL1 comprises DIQLTQSPSSLSASVGDRVTITC (SEQ ID NO:26);

FRL2 comprises WYQQKPGKAPKLLIY (SEQ ID NO:27);

FRL3 comprises GVP(S or D)RFSGS(G or V) SGTDFTFTISSLQPEDIATYYC (SEQ ID NO:28);

FRL4 comprises FGQGTKVEIK (SEQ ID NO:29);

FRH1 comprises EVQLVESGGGVVQPG RSLRLSCSSSGFDFT (SEQ ID NO:30), or EVQLVESGGG VVQPGRSLRLSCSASGFDFT (SEQ ID NO:31);

FRH2 comprises WVRQAPGKGLEWVA (SEQ ID NO:33);

FRH3 comprises RFTIS RDNSKNTLFLQMDSLRPEDTGVYFCAS (SEQ ID NO:36), or RFTISRDNAKNTLFLQMDSLRPEDTGVYFCAS (SEQ ID NO:37); and FRH4 comprises WGQGTPVTVSS (SEQ ID NO:39);

and wherein may be in the sulfhydryl or disulfide form.

12. The method of claim 1, wherein said humanized mAb heavy and light chain variable regions are KLHuVHAIG/HuVK (SEQ ID NO:13/SEQ ID NO:19), KLHuVHAIGA/HuVK (SEQ ID NO:14/SEQ ID NO:19) or KLHuVHAIGAY/HuVK (SEQ ID NO:15/SEQ ID NO:19).

13. The method of claim 1, wherein said humanized mAb heavy and light chain variable regions are KLHuVHAIGA/HuVK (SEQ ID NO:14/SEQ ID NO:19).

14. A method for diagnosing a patient comprising administering a conjugate to said patient in an effective amount for diagnosis, wherein said conjugate comprises:

a diagnostic agent bound to a humanized Class III, anti-CEA, monoclonal antibody (mAb) or a fragment thereof, wherein the complementarity-determining regions (CDRs) of said humanized mAb are CDRs from a parental murine Class III, anti-CEA mAb, wherein the light chain variable region comprises CDRL1 comprising KASQDVGTSVA (SEQ ID NO:20), CDRL2 comprising WTSTRHT (SEQ ID NO:21), and CDRL3 comprising QQYSLYRS (SEQ ID NO:22), and the heavy chain variable region comprises CDRH1 comprising TYWMS (SEQ ID NO:23), CDRH2 comprising EIHPDSSTINYAPSLKD (SEQ ID NO:24) and CDRH3 comprising LYFGFPWFAY (SEQ ID NO:25), and each of the framework regions (FRs) of the light and heavy chain variable regions is from a human antibody, wherein said humanized mAb retains the binding specificity of said parental murine Class III, anti-CEA mAb.

15. The method of claim 14, wherein said diagnostic agent comprises an imaging agent.

16. The method of claim 15, wherein said imaging agent is a radionuclide or a metal chelator complexed radionuclide.

17. The method of claim 16, wherein said radionuclide is iodine, yttruim or technetium.

18. The method of claim 17, wherein said radionuclide is $^{131}$I.

19. The method of claim 14, wherein:

(a) the light chain variable regions correspond to the formula:

FRL1-CDRL1-FRL2-CDRL2-FRL3-CDRL3-FRL4, wherein each FR is a different framework region of a human antibody, and FRL1 comprises a region of about 23 amino acids that occurs naturally in the FRL1 of a human antibody;

FRL2 comprises a region of about 15 amino acids that occurs naturally in the FRL2 of a human antibody;

FRL3 comprises a region of about 32 amino acids that occurs naturally in the FRL3 of a human antibody;

FRL4 comprises a region of about 10 amino acids that occurs naturally in the FRL4 of a human antibody; and (b) the heavy chain variable regions corresponds to the formula:

FRH1-CDRH1-FRH2-CDRH2-FRH3-CDRH3-FRH4, wherein each FR is a different framework region of a human antibody, and FRH1 comprises a region of 28–32 amino acids that occurs naturally in the FRH1 of a human antibody;

FRH2 comprises a region of 12–16 amino acids that occurs naturally in the FRH2 of a human antibody;

FRH3 comprises a region of 30–34 amino acids that occurs naturally in the FRH3 of a human antibody; and FRH4 comprises a region of 9–13 amino acids that occurs naturally in the FRH4 of a human antibody.

20. The method of claim 19, wherein

FRL1 comprises DIQLTQSPSSLSASVGDRVTITC (SEQ ID NO:26);

FRL2 comprises WYQQKPGKAPKLLIY (SEQ ID NO:27);

FRL3 comprises GVP(S or D)RFSGS(G or V)SGTDFTFTISSLQPEDLATYYC (SEQ ID NO:28);

FRL4 comprises FGQGTKVEIK (SEQ ID NO:29);

FRH1 comprises EVQLVESGGGVVQPG RSLRLSCSSSGFDFT (SEQ ID NO:30), or EVQLVESGGG VVQPGRSLRLSCSASGFDFT (SEQ ID NO:31);

FRH2 comprises WVRQAPGKGLEWVA (SEQ ID NO:33);

FRH3 comprises RFTIS RDNSKNTLFLQMDSLRPEDTGVYFCAS (SEQ ID NO:36), or RFTISRDNAKNTLFLQMDSLRPEDTGVYFCAS (SEQ ID NO:37); and FRH4 comprises WGQGTPVTVSS (SEQ ID NO:39);

and wherein C may be in the sulfhydryl or disulfide form.

21. The method of claim 14, wherein said humanized mAb heavy and light chain variable regions are KLHuVHAIG/HuVK (SEQ ID NO:13/SEQ ID NO:19), KLHuVHAIGA/HuVK (SEQ ID NO:14/SEQ ID NO:19) or KLHuVHAIGAY/HuVK (SEQ ID NO:15/SEQ ID NO:19).

22. The method of claim 14, wherein said humanized mAb heavy and light chain variable regions are KLHuVHAIGA/HuVK (SEQ ID NO:14/SEQ ID NO:19).

23. A method for treating a patient comprising administering a humanized Class III, anti-CEA, monoclonal antibody (mAb) to said patient in an effective amount for treatment, wherein said mAb comprises:

a humanized Class III, anti-CEA, monoclonal antibody (mAb), wherein the complementarity-determining regions (CDRs) of said humanized mAb are CDRs from a parental murine Class III, anti-CEA mAb or a fragment thereof, wherein the light chain variable region comprises CDRL1 comprising KASQDVGTSVA (SEQ ID NO:20), CDRL2 comprising WTSTRHT (SEQ ID NO:21), and CDRL3 comprising QQYSLYRS (SEQ ID NO:22), and the heavy chain variable region comprises CDRH1 comprising TYWMS (SEQ.ID) NO:23), CDRH2 comprising EIHPDSSTINYAPSLKD (SEQ ID NO:24) and CDRH3 comprising LYFGFPWFAY (SEQ ID NO:25), and each of the framework regions (FRs) of the light and heavy chain variable regions is from a human antibody, wherein said humanized mAb retains the binding specificity of said parental murine Class III, anti-CEA mAb.

24. The method of claim 23, wherein:
(a) the light chain variable regions are characterized by the formula:

FRL1-CDRL1-FRL2-CDRL2-FRL3-CDRL3-FRL4, wherein each FR is a different framework region of a human antibody, and FRL1 comprises a region of about 23 amino acids that occurs naturally in the FRL1 of a human antibody;
FRL2 comprises a region of about 15 amino acids that occurs naturally in the FRL2 of a human antibody;
FRL3 comprises a region of about 32 amino acids that occurs naturally in the FRL3 of a human antibody;
FRL4 comprises a region of about 10 amino acids that occurs naturally in the FRL4 of a human antibody; and
(b) the heavy chain variable regions are characterized by the formula:

FRH1-CDRH1-FRH2-CDRH2-FRH3-CDRH3-FRH4, wherein each FR is a different framework region of a human antibody, and FRH1 comprises a region of 28–32 amino acids that occurs naturally in the FRH1 of a human antibody;
FRH2 comprises a region of 12–16 amino acids that occurs naturally in the FRH2 of a human antibody;
FRH3 comprises a region of 30–34 amino acids that occurs naturally in the FRH3 of a human antibody; and
FRH4 comprises a region of 9–13 amino acids that occurs naturally in the FRH4 of a human antibody.

25. The method of claim 24, wherein
FRL1 comprises DIQLTQSPSSLSASVGDRVTITC (SEQ ID NO:26);
FRL2 comprises WYQQKPGKAPKLLIY (SEQ ID NO:27);
FRL3 comprises GVP(S or D)RFSGS(G or V)SGTDFTFTISSLQPEDJATYYC (SEQ ID NO:28);
FRL4 comprises FGQGTKVEIK (SEQ ID NO:29);
FRH1 comprises EVQLVESGGG VQPGRSLRLSCSSSGFDFT (SEQ ID NO:30), or EVQLVESGGGVVQPGRSLRLSCSASGFDFT (SEQ ID NO:31);
FRH2 comprises WVRQAPGKGLEWVA (SEQ ID NO:33);
FRH3 comprises RFTISRDNSKNTLFLQMDSLRPEDTGVYFCAS (SEQ ID NO:36), or RFTISRDNAKNTLFLQMDSLRPEDTGVYFC AS (SEQ ID NO:37); and
FRH4 comprises WGQGTPVTVSS (SEQ ID NO:39);
and wherein C may be in the suithydryl or disulfide form.

26. The method of claim 23, wherein said humanized mAb heavy and light chain variable regions are KLHuVHAIG/HuVK (SEQ ID NO:13/SEQ ID NO:19), KLHIuVHAIGA/HuVK (SEQ ID NO:14/SEQ ID NO:19) or KLHuVHAIGAY/HuVK (SEQ ID NO:15/SEQ ID NO:19).

27. The method of claim 23, wherein said humanized mAb heavy and light chain variable regions are KLHuVHAIGA/HuVK (SEQ ID NO:14/SEQ ID NO:19).

* * * * *